US008263064B2

(12) United States Patent
Karin et al.

(10) Patent No.: US 8,263,064 B2
(45) Date of Patent: Sep. 11, 2012

(54) METHOD OF SUPPRESSING DISEASE SEVERITY OF MULTIPLE SCLEROSIS USING CHEMOKINE CXC11

(75) Inventors: Nathan Karin, Haifa (IL); Yaniv Zohar, Kiryat-Haim (IL); Gizi Wildbaum, Kiryat Yam (IL)

(73) Assignee: Rappaport Family Institute for Research in the Medical Sciences, Haifa (IL)

(*) Notice: Subject to any disclaimer, the term of this patent is extended or adjusted under 35 U.S.C. 154(b) by 70 days.

(21) Appl. No.: 12/602,771

(22) PCT Filed: Jun. 4, 2008

(86) PCT No.: PCT/IL2008/000757

§ 371 (c)(1),
(2), (4) Date: Dec. 3, 2009

(87) PCT Pub. No.: WO2008/149354

PCT Pub. Date: Dec. 11, 2008

(65) Prior Publication Data

US 2010/0196406 A1 Aug. 5, 2010

Related U.S. Application Data

(60) Provisional application No. 60/924,866, filed on Jun. 4, 2007.

(51) Int. Cl.
*A61K 38/19* (2006.01)

(52) U.S. Cl. ........................................ 424/85.1; 514/1.1

(58) Field of Classification Search ........................ None
See application file for complete search history.

(56) References Cited

U.S. PATENT DOCUMENTS

| | | | | |
|---|---|---|---|---|
| 5,116,964 | A * | 5/1992 | Capon et al. | 536/23.5 |
| 5,756,084 | A | 5/1998 | Honjo et al. | |
| 6,140,064 | A | 10/2000 | Loetscher et al. | |
| 6,355,252 | B1 | 3/2002 | Smith et al. | |
| 6,686,175 | B1 | 2/2004 | Loetscher et al. | |
| 6,723,538 | B2 | 4/2004 | Mack et al. | |
| 6,843,991 | B1 | 1/2005 | Efstathiou et al. | |
| 6,869,606 | B1 | 3/2005 | Newman et al. | |
| 7,259,000 | B2 | 8/2007 | Dinchuk et al. | |
| 2002/0071849 | A1 | 6/2002 | Smith et al. | |
| 2003/0017979 | A1 | 1/2003 | Mack et al. | |
| 2003/0103938 | A1 | 6/2003 | Jinquan et al. | |
| 2005/0191293 | A1 | 9/2005 | Deshpande et al. | |
| 2005/0191702 | A1 | 9/2005 | Mack et al. | |
| 2006/0257359 | A1 | 11/2006 | Francois et al. | |

FOREIGN PATENT DOCUMENTS

| | | |
|---|---|---|
| AU | 2003204344 | 12/2003 |
| WO | WO 97/07198 | 2/1997 |
| WO | WO 00/18431 | 4/2000 |
| WO | WO 01/37872 | 5/2001 |
| WO | WO 01/72830 | 10/2001 |
| WO | WO 03/106488 | 12/2003 |
| WO | WO 2004/019046 | 3/2004 |
| WO | WO 2005/016241 | 2/2005 |
| WO | WO 2005/049799 | 6/2005 |
| WO | WO 2005/103722 | 11/2005 |
| WO | WO 2006/125077 | 11/2006 |
| WO | WO 2007/094005 | 8/2007 |
| WO | WO 2008/096359 | 8/2008 |
| WO | WO 2008/146272 | 12/2008 |
| WO | WO 2008/149354 | 12/2008 |

OTHER PUBLICATIONS

Beers and Berkow. (1999). The Merck Manual of Diagnosis and Therapy, 17 th edition, pp. 1474-1476.*

International Search Report and the Written Opinion Dated Jul. 6, 2010 From the International Searching Authority Re.: Application No. PCT/IL2010/000199.

Trotta et al. "Modelling of the Membrane Receptor CXCR3 and Its Complexes With CXCL9, CXCL10 and CXCL11 Chemokines: Putative Target for New Drug Design", Molecular Immunology, XP026886952, 47(2-3): 332-339, Dec. 1, 2009. Abstract.

Xanthou et al. "Molecualr Characterization of the Chemokine Receptor CXCR3: Evidence for the Involvement of Distinct Extracellular Domains in a Multi-Step Model of Ligand Binding and Receptor Activation", European Journal of Immunology, XP002587427, 33(10): 2927-2936, Oct. 2003. Abstract, Figs.3, 5B, 5E, Table 1.

Ytterberg et al. "Combination Therapy With Interferon-Beta and Glatiramer Acetate in Multiple Sclerosis", Acta Neurologica Scandinavica, XP002587426, 116(2): 96-99, Aug. 2007. Abstract.

Colvin et al. "CXCR3 Requires Tyrosine Sulfation for Ligand Binding and a Second Extracellular Loop Arginine Residue for Ligand-Induced Chemotaxis", Molecular and Cellular Biology, XP002587428, 26(15): 5838-5849, Aug. 2006.

Hamilton et al. "IFN-γ Regulates Murine Interferon-Inducible T Cell Alpha Chemokine (I-TAC) Expression in Dendritic Cell Lines and During Experimental Autoimmune Encephalomyelitis", Scandinavian Journal of Immunology, 55(2): 171-177, 2002. Abstract.

Lazzeri et al. "CXCR3-Binding Chemokines: Novel Multifunctional Therapeutic Targets", Current Drug Targets—Immune, Endocrine & Metabolic Disorders, XP009053456, 5(1): 109-118, Jan. 1, 2005. Abstract, p. 115, Fig. 2.

Lee et al. "CXCL10 and Autoimmune Diseases", Autoimmunity Reviews, 8(5): 379-383, Mar. 2009. Abstract.

Nakae et al. "Phenotypic Differences Between Th1 and Th17 Cells and Negative Regulation of Th1 Cell Differentiation by IL-17", Journal of Leukocyte Biology, 81: 125801268, May 2007.

Nanki et al. "Cutting Edge: Stromal Cell-Derived Factor-1 Is a Costimulator for CD4+ T Cell Activation", The Journal of Immunology, XP002195353, 164: 5010-5014, Jan. 1, 2000.

Schulthess et al. "CXCL10 Impairs β Cell Function and Viability in Diabetes Through TLR4 Signaling", Cell Metabolism, 9(2): 125-139, Feb. 2009. Abstract.

(Continued)

*Primary Examiner* — Prema Mertz

(74) *Attorney, Agent, or Firm* — John P. White; Cooper & Dunham LLP

(57) ABSTRACT

A method of treating an autoimmune disease such as Multiple Sclerosis is disclosed. The method comprises administering to a subject a therapeutically effective amount of CXCL11. Polypeptides and pharmaceutical compositions for treating same are also disclosed.

5 Claims, 10 Drawing Sheets

OTHER PUBLICATIONS

Sørensen et al. "Multiple Sclerosis: A Study of CXCL10 and CXCR3 Co-Localization in the Inflamed Central Nervous System", Journal of Neuroimmunology, 127(1-2): 59-68, Jun. 2002. Abstract.
Szczuciński et al. "CXCL11 (Interferon-Inducible T-Cell Alpha Chemoattractant) and Interleukin-18 in Relapsing-Remitting Multiple Sclerosis Patients Treated With Methylprednisolone", European Neurology, XP009107475, 58(4): 228-232, Jan. 1, 2007. Abstract, p. 231, Right-Sided Col., § 3.
Communication Relating to the Results of the Partial International Search Dated Sep. 17, 2008 From the International Searching Authority Re.: Application No. PCT/IL2008/000663.
Communication Relating to the Results of the Partial International Search Dated Feb. 20, 2009 From the International Searching Authority Re.: Application No. PCT/IL2008/000757.
International Preliminary Report on Patentability Dated Oct. 16, 2009 From the International Preliminary Examining Authority Re.: Application No. PCT/IL2008/000757.
International Preliminary Report on Patentability Dated Aug. 20, 2009 From the International Bureau of WIPO Re.: Application No. PCT/IL2008/000166.
International Preliminary Report on Patentability Dated May 20, 2009 From the International Preliminary Examining Authority Re.: Application No. PCT/IL2008/000663.
International Search Report Dated Jun. 4, 2009 From the International Searching Authority Re.: Application No. PCT/IL2008/000757.
International Search Report Dated Aug. 11, 2008 From the International Searching Authority Re.: Application No. PCT/IL2008/000166.
International Search Report Dated Nov. 13, 2008 From the International Searching Authority Re.: Application No. PCT/IL2008/000663.
Written Opinion Dated Jun. 4, 2009 From the International Searching Authority Re.: Application No. PCT/IL2008/000757.
Written Opinion Dated Aug. 11, 2008 From the International Searching Authority Re.: Application No. PCT/IL2008/000166.
Written Opinion Dated Nov. 13, 2008 From the International Searching Authority Re.: Application No. PCT/IL2008/000663.
Burdick et al. "CXCL11 Attenuates Bleomycin-Induced Pulmonary Fibrosis Via Inhibition of Vascular Remodelling", American Journal of Respiratory and Critical Care Medicine, 171: 261-268, 2005.
Clark-Lewis et al. "Structure-Function Relationship Between the Human Chemokine Receptor CXCR3 and Its Ligands", The Journal of Biological Chemistry, 278(1): 289-295, 2003.
Colvin et al. "CXCR3 Requires Tyrosine Sulfation for Ligand Binding and a Second Extracellular Loop Arginine Residue for Ligand-Induced Chemotaxis", Molecular and Cellular Biology, 26(15): 5838-5849, Aug. 2006.
Colvin et al. "Intracellular Domains of CXCR3 That Mediate CXCL9, CXCL10, and CXCL11 Function", The Journal of Biological Chemistry, 279(29): 30219-30227, Jul. 16, 2004.
Dalton et al. "Immunomonitoring of Renal Translplant Recipients in the Early Posttransplant Period by Sequential Analysis of Chemokine and Chemokine Receptor Gene Expression in Peripheral Blood Mononuclear Cells", Transplantation Proceedings, 37(2): 747-751, Mar. 2005. Abstract.
Engwerda "Immunology and Infection in Malaria", Infectious Diseases & Immunology Division, QIMR Website, Jul. 9, 2009. Abstract.
Goldberg-Bittman et al. "The Expression of the Chemokine Receptor CXCR3 and Its Ligand, CXCL10, in Human Breast Adenocarcinoma Cell Lines", Immunology Letters, 92(1-2): 171-178, Mar. 2004. Abstract.
Hensbergen et al. "The CXCR3 Targeting Chemokine CXCL11 Has Potent Antitumor Activity in Vivo Involving Attraction of CD8+ T Lymphocytes But Not Inhibition of Angiogenesis", Journal of Immunotherapy, 28(4): 343-351, Jul./Aug. 2005. Abstract.
Huang et al. "Human Trophoblasts Recruited T Lymphocytes and Monocytes Into Decidua by Secretion of Chemokine CXCL16 and Interaction With CXCR6 in the First-Trimester Pregnancy", The Journal of Immunology, XP002494525, 180(4): 2367-2375, Feb. 15, 2008.
Jiang et al. "Cutting Edge: Critical Role of CXCL16/CXCR6 in NKT Cell Trafficking in Allograft Tolerance", Journal of Immunology, XP002494523, 175(4): 2052-2055, Aug. 15, 2005. Abstract, p. 2052, 1-h Col., § 2.
Kawada et al. "Pivotal Role of CXCR3 in Melanoma Cell Metastasis to Lymph Nodes", Cancer Research, 64: 4010-4017, Jun. 1, 2004.
Kremer et al. "Haplotype-Independent Costimulation of IL-10 Secretion by SDF-1/CXCL12 Proceeds Via AP-1 Binding to the Human IL-10 Promoter", The Journal of Immunology, XP002489942, 178(3): 1581-1588, Feb. 1, 2007.
Shimaoka et al. "Cell Surface-Anchored SR-PSOX/CXC Chemokine Ligand 16 Mediated Firm Adhesion of CXC Chemokine Receptor 6-Expressing Cells", Journal of Leukocyte Biology, XP009063730, 75(2): 267-274, Feb. 2004.
Szczucinski et al. "Chemokines and Chemokine Receptors in Multiple Sclerosis. Potential Targets for New Therapies", Acta Neurologica Scandinavica, XP002501896, 115(3): 137-146, Mar. 2007.
Szczucitiski et al. "CXCL11 (Interferon-Inducible T-Cell Alpha Chemoattractant) and Interleukin-18 in Relapsing-Remitting Multiple Sclerosis Patients Treated With Methylprednisolone", European Neurology, XP009107475, 58(4): 228-232, Jan. 1, 2007. Abstract, p. 231, Right-Sided Col., § 3.
Wenzel et al "Inflammation in Cutaneous Lichenoid Graft-Versus-Host Disease", Journal of the American Academy of Dermatology, 58(3): 437-442, Mar. 2008. Abstract.
Wilbanks et al. "Expression Cloning of the STRL33/BONZO/TYMSTR Ligand Reveals Elements of CC, CXC, and CX3C Chemokines", Journal of immunology, XP002494524, 166(8): 5145-5154, Apr. 15, 2001. Abstract, p. 5146.
Zipin-Roitman et al. "CXCL20 Promotes Invasion-Related Properties in Human Colorectal Carcinoma Cells", Cancer Research, 67(7): 3396-3405, Apr. 1, 2007.

* cited by examiner

METHOD OF SUPPRESSING DISEASE SEVERITY OF MULTIPLE SCLEROSIS USING CHEMOKINE CXC11

RELATED APPLICATIONS

This application is a National Phase Application of PCT Patent Application No. PCT/IL2008/000757 having International Filing Date of Jun. 4, 2008, which claims priority from U.S. Provisional Patent Application No. 60/924,866, filed on Jun. 4, 2007. The contents of the above Application are all incorporated herein by reference.

FIELD AND BACKGROUND OF THE INVENTION

The present invention relates to the use of CXCL11 for the treatment of inflammatory diseases in general and Multiple Sclerosis in particular.

Chemokines constitute a family of small structurally cytokine-like, secreted proteins that regulate cell trafficking. They are produced and secreted by a wide variety of cell types in response to early inflammatory mediators, such as IL-1$\beta$ or TNF-$\alpha$, and in response to bacterial or viral infection. Chemokines function mainly as chemoattractants for leukocytes, recruiting monocytes, neutrophils and other effector cells from the blood to sites of infection or damage. They can be released by many different cell types (e.g. macrophages) and can mediate a range of pro-inflammatory effects on leukocytes, such as triggering of chemotaxis, degranulation, synthesis of lipid mediators, and integrin activation.

Chemokines can be subdivided into four classes, the C, C—C, C—X—C and C—X3-C chemokines, depending on the number and arrangement of the conserved amino-terminal cysteine motifs, where "X" is a nonconserved amino acid residue. The interaction of these soluble proteins with their specific receptors, which belong to the superfamily of seven-transmembrane domain G-protein-coupled receptors (GPCRs), mediate their biological effects resulting in, among other responses, rapid increase in intracellular calcium concentration, changes in cell shape, increased expression of cellular adhesion molecules, degranulation, and promotion of cell migration.

The chemokine receptor CXCR3, also referred to as G protein-coupled receptor 9 (GPR9) and CD183, is predominantly expressed on inflammatory effector T cells, including Th1 cells [Qin et al., J Clin Invest (1998) 101:746-54; Sallusto et al., J Exp Med (1998) 187:875-83] as well as the newly defined IL-17 producing $Th_{17}$ cells [Nakae et al., J Leukoc Biol (2007) 81:1258-68], but is also expressed on other lymphocytes, including B cells and NK cells [Sallusto et al., supra]. CXCR3 is highly induced following cell activation. Three chemokine ligands compete for binding to this receptor: CXCL9 (MIG), CXCL10 (IP-10) and CXCL11 (I-TAC) [Colvin et al., J Biol Chem (2004) 279:30219-27]. These ligands bind different epitopes on CXCR3, yet CXCL11 binds CXCR3 with higher affinity than CXCL9 and CXCL10 [Cole et al., supra; Tensen et al., J. Invest. Derm. (1999) 112:716-722]. CXCL11 may antagonize the function of the other two CXCR3 ligands since it rapidly leads to receptor internalization, which thus becomes inaccessible to the other CXCR3 ligands [Colvin et al., supra].

Multiple sclerosis (MS) is an inflammatory, demyelinating disease of the central nervous system (CNS). MS and its animal model, experimental autoimmune encephalomyelitis (EAE), are believed to result from autoimmune mediated activated immune cells, such as T- and B-lymphocytes as well as macrophages and microglia, and is considered to be an inflammatory neurodegenerative disease. Pathologically, MS is characterized by perivenous infiltration of lymphocytes and macrophages into the CNS parenchyma, resulting in demyelinative lesions termed plaques. These plaques, which are the hallmark of MS, are associated with oligodendrocytes death, axonal damage and neuronal loss. The inflammatory cell recruitment from the vascular bed to the perivascular space, and from there on to the CNS parenchyma, is the result of a multi-step process, which is orchestrated in part by chemokines.

CXCR3 has been previously implicated in the pathogenesis of MS [Sorensen et al., J Clin Invest. (1999) 103(6):807-15]. CXCR3 has been shown to be expressed on lymphocytic cells in virtually every perivascular inflammatory infiltrate in active MS lesions [Sorensen et al., supra]. Furthermore, elevated levels of the two CXCR3 ligands, CXCL9 and CXCL10, were found in the cerebrospinal fluid (CSF) of subjects during MS attacks which are probably accountable for the chemoattraction of CXCR3 expressing cells (e.g. $CD4^+$ T cells) from the blood circulation into the site of inflammation [Balashov et al. Proc Natl Acad Sci USA (1999) 96:6873-8; Sorensen et al., supra]. Additionally, in EAE induced mice, administration of anti-CXCL10 antibodies decreased clinical and histological disease incidence, severity, as well as infiltration of mononuclear cells and Th1 cells into the CNS [Fife et al, J Immunol (2001) 166:7617-24]. Taken together, these findings provide strong cumulative evidence supporting a pivotal role for CXCR3/CXCL10/CXCL9 axis in T cell recruitment to the brain in MS. Yet the role the CXCR3/CXCL11 axis plays in MS is still vague.

There is substantial evidence to support the hypothesis that CXCL11 is involved in MS pathogenesis. For example, Hamilton et al. have shown elevated levels of murine I-TAC mRNA in CNS of EAE induced mice [Hamilton et al., Scand J Immunol. (2002) 55(4171-7].

Lazzeri and Romagnani have proposed the chemokine CXCL11 as a possible therapeutic target in multiple sclerosis, however, they in fact teach away from using CXCL11 for MS treatment as they propose treatment of MS by using drugs that block CXCL11 activity [Lazzeri E. and Romagnani P., Curr Drug Targets Immune Endocr Metabol Disord. (2005) 5(1): 109-18].

Clark-Lewis et al. constructed a potent antagonist for the CXCR3 receptor which enabled them to explore the structure-function relationship of CXCR3 with its ligands, in particular I-TAC. The antagonist was obtained by NH(2)-terminal truncation of I-TAC. This molecule (I-TAC (4-73)), lacked the first three residues and was shown to comprise no agonistic activity. Instead it was shown to compete with I-TAC for the binding to CXCR3-bearing cells, inhibiting cell migration and inhibiting calcium changes in CXCR3 expressing cells in response to stimulation with CXCR3 chemokines. The I-TAC antagonist was not contemplated for therapeutics [Clark-Lewis et al., J Biol Chem. (2003) 278(1):289-95].

U.S. Pat. No. 6,869,606 discloses biotinylated-I-TAC complexes which maintain their functionality (e.g., binding to CXCR3 and inducing chemotaxis). U.S. Pat. No. 6,869,606 does not mention Multiple Sclerosis as a potential target disease for such complexes.

U.S. Publication No. 20060257359 discloses means of modulating phenotypes of macrophage related cells for the treatment of diseases, such as Multiple Sclerosis. U.S. Publication No. 20060257359 teaches that modulation of the cellular phenotype may be accomplished by introducing effectors (e.g., proteins, antibodies or RNA molecules) to macrophage related cells thereby altering gene expression and cell phenotype (e.g., secretion of cytokines or cell migration). Amongst a long list of potential effectors, I-TAC is specified therein. U.S. Publication No. 20060257359 describes treatment of a great number of autoimmune diseases yet it does not specify which diseases may be alleviated by up-regulation or down-regulation of I-TAC. In addition, U.S. Publication No. 20060257359 does not provide any experimental support to indicate treatment of MS with I-TAC.

PCT Publication No. WO06125077 discloses a non-natural CXCR3 polypeptide receptor ligand wherein the N-loop domain is from I-TAC for treatment of fibrotic disorders, angiogenic disorders and cancer. Treatment of MS was not contemplated.

PCT Publication No. WO05016241 discloses a synthetic CXCR3 polypeptide ligand for treating fibrotic disorders, angiogenic disorders, cancer and bacterial infections. This invention describes the use of I-TAC consensus sequence (amino acid residues which occur in I-TAC) which include or lack a signaling sequence. Thus, such CXCR3 polypeptides may function as agonist or antagonists of CXCR3. Treatment of MS was not contemplated.

There is thus a widely recognized need for, and it would be highly advantageous to have CXCL11 polypeptides that can be used in the treatment of Multiple Sclerosis.

SUMMARY OF THE INVENTION

According to one aspect of the present invention there is provided a method of treating an autoimmune disease in a subject in need thereof, the method comprising administering to the subject a therapeutically effective amount of CXCL11, thereby treating the autoimmune disease in the subject.

According to another aspect of the present invention there is provided a method of treating Multiple Sclerosis in a subject in need thereof, the method comprising administering to the subject a therapeutically effective amount of CXCL11, thereby treating Multiple Sclerosis in the subject.

According to yet another aspect of the present invention there is provided a use of CXCL11 for the manufacture of a medicament identified for treating an autoimmune disease.

According to yet another aspect of the present invention there is provided a method of treating an autoimmune disease in a subject in need thereof, the method comprising ex vivo contacting T cells with CXCL11 under conditions which result in generation of regulatory T cells and administering the regulatory T cells to the subject, thereby treating the autoimmune disease in the subject.

According to yet another aspect of the present invention there is provided a method of treating Multiple Sclerosis in a subject in need thereof, the method comprising ex vivo contacting T cells with CXCL11 under conditions which result in generation of regulatory T cells and administering the regulatory T cells to the subject, thereby treating Multiple Sclerosis in the subject.

According to yet another aspect of the present invention there is provided a use of T cells ex vivo cultured with CXCL11 for the manufacture of a medicament identified for treating an autoimmune disease.

According to further features in preferred embodiments of the invention described below the T cells are obtained from the subject.

According to still further features in the described preferred embodiments the T cells are obtained from a donor.

According to still further features in the described preferred embodiments the donor is allogeneic with respect to the subject.

According to still further features in the described preferred embodiments the donor is syngeneic with respect to the subject.

According to still further features in the described preferred embodiments the T cells are CD4+ T cells.

According to still further features in the described preferred embodiments the regulatory T cells are specifically selected prior to administering to the subject.

According to still further features in the described preferred embodiments the conditions which result in generation of regulatory T cells further comprise stimulation with an antigen.

According to still further features in the described preferred embodiments the antigen is anti-CD3ε mAb.

According to still further features in the described preferred embodiments the antigen is anti-CD28 mAb.

According to still further features in the described preferred embodiments the regulatory T cells secrete IL-10.

According to still further features in the described preferred embodiments the regulatory T cells secrete IL-4.

According to still another aspect of the present invention there is provided an article of manufacture comprising CXCL11 and an anti-Multiple Sclerosis agent being packaged in a packaging material and identified in print, in or on the packaging material for use in the treatment of Multiple Sclerosis.

According to an additional aspect of the present invention there is provided an isolated polypeptide comprising an amino acid sequence as set forth in SEQ ID NO: 6.

According to yet an additional aspect of the present invention there is provided a pharmaceutical composition comprising as an active ingredient the isolated polypeptide comprising an amino acid sequence as set forth in SEQ ID NO: 6 and a pharmaceutically acceptable carrier.

According to still an additional aspect of the present invention there is provided a use of the isolated polypeptide comprising an amino acid sequence as set forth in SEQ ID NO: 6, for the manufacture of a medicament identified for treating an inflammatory disease.

According to still further features in the described preferred embodiments, the CXCL11 is capable of up-regulating secretion of IL-10 and/or IL-4 from macrophages and T cells.

According to still further features in the described preferred embodiments the CXCL11 is capable of down-regulating secretion of a cytokine from macrophages and T cells, wherein the cytokine is selected from the group consisting of TNF-α, IFN-γ, IL-2 and IL-12.

According to still further features in the described preferred embodiments the CXCL11 is capable of CXCR3 receptor down-regulation.

According to still further features in the described preferred embodiments the inflammatory disease is an autoimmune disease.

According to still further features in the described preferred embodiments the autoimmune disease is selected from the group consisting of rheumatoid arthritis, rheumatoid spondylitis, osteoarthritis, gouty arthritis, arthritic conditions, inflamed joints, eczema, inflammatory skin conditions, inflammatory eye conditions, conjunctivitis, pyresis, tissue necrosis resulting from inflammation, tissue rejection following transplant surgery, Crohn's disease and ulcerative colitis, airway inflammation, asthma, bronchitis, systemic lupus erythematosis, multiple sclerosis, myasthenia gravis, progressive systemic sclerosis, atopic dermatitis, hyperimmunoglobin E, hepatitis B antigen negative chronic active hepatitis, Hashimoto's thyroiditis, familial Mediterranean fever, Grave's disease, autoimmune haemolytic anemia, primary biliary cirrhosis, inflammatory bowel disease, viral infections, HIV infections and AIDS.

According to still further features in the described preferred embodiments the autoimmune disease is Multiple Sclerosis.

According to still further features in the described preferred embodiments, an amino acid sequence of the CXCL11 is attached to a heterologous amino acid sequence.

According to still further features in the described preferred embodiments the method further comprises administering to the subject an additional anti-Multiple Sclerosis agent.

According to still further features in the described preferred embodiments the anti-Multiple Sclerosis agent is selected from the group consisting of Interferon Beta 1a, Interferon Beta 1b, Glatiramer Acetate, Mitoxantrone, MethylPrednisolone, Prednisone, Prednisolone, Dexamethasone, Adreno-corticotrophic Hormone (ACTH) and Corticotropin.

The present invention successfully addresses the shortcomings of the presently known configurations by providing a novel means of treating inflammatory diseases.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A shows selectivity of binding of each of the DNA-vaccination based antibodies to each of the three CXCR3 ligands; CXCL9, CXCL10 and CXCL11 as detected by ELISA. Results of triplicates are shown as mean OD (450 nm)±SE. FIG. 1B shows neutralization of chemotaxis by each of the DNA-vaccination based antibodies using a Trans-well migration assay. The ability of each antibody to inhibit the chemokine-induced migration of CXCR3+ cells (MOG specific CD4+ Th1 line constructed by the present inventor) by each chemokine was measured. Results of triplicate measurements were analyzed by flow cytometry and are shown as mean relative cell number±SE.

FIG. 5A shows TNF-α secretion; FIG. 5B shows IFN-γ secretion; FIG. 5C shows IL-12 secretion; FIG. 5D shows IL-2 secretion; FIG. 5E shows IL-4 secretion; and FIG. 5F shows IL-10 secretion. Results of triplicates are shown as mean cytokine level±SE.

FIG. 7A shows IL-10 secretion; FIG. 7B shows IL-4 secretion; FIG. 7C shows IFN-γ secretion; FIG. 7D shows TNF-α secretion; and FIG. 7E shows TGF-β secretion. Results of triplicates are shown as mean cytokine level±SE.

FIG. 8A shows control $MOG_{35-55}$ activated spleen cells. FIG. 8B shows $MOG_{35-55}$ activated spleen cells that were co-cultured with CXCL11-IgG.

FIGS. 10A-F show ex-vivo cytokines production by primary T cell cultures in response to the target antigen ($MOG_{35-55}$) Primary T cells were isolated from EAE induced mice (on day 9) and were further cultured for 72 hours with MOG35-55 (50 μg/ml) in the presence of either rmCXCL10 or rmCXCL11 (50 ng/ml). TNF-α (FIG. 10A), IFN-γ (FIG. 10B), IL-12 (FIG. 10C), IL-2 (FIG. 10D), IL-4 (FIG. 10E) and IL-10 (FIG. 10F) cytokine levels in the culture media were determined by ELISA according to the manufacturer's protocol. Results are shown as mean level±SE; FIGS. 10G-K show ex-vivo cytokine production by naïve CD4+ T cells. Naïve CD4+ T cells were purified from mice spleens using magnetic beads and were stimulated (300,000 cell/ml) for 48 hours with immobilized anti-CD3ε mAb and soluble anti-CD28 mAb in the presence of either rmCXCL10 or rmCXCL11 (50 ng/ml). TNF-α (FIG. 10G), IFN-γ (FIG. 10H), IL-2 (FIG. 10I), IL-4 (FIG. 10J) and IL-10 (FIG. 10K) cytokine levels in the culture media were determined by ELISA according to manufacturer's protocol. Results are shown as mean level±SE.

DESCRIPTION OF THE PREFERRED EMBODIMENTS

The present invention is of methods of treating autoimmune disorders, such as Multiple Sclerosis using CXCL11 and pharmaceutical compositions comprising same.

The principles and operation of the methods and compositions according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Traditionally chemokines has been looked at mostly as pro-inflammatory mediators that attract inflammatory leucocytes, particularly effector T cells and activated monocytes to sites of inflammation, and therefore many of them and their seven-transmembrane, G protein-coupled receptors have been major targets for therapy of inflammatory autoimmune diseases.

CXCL9, CXCL10 and CXCL11 are all potent chemokines that mediate their activities by binding to a common receptor named CXCR3. Whilst there is strong cumulative evidence suggesting that both CXCL9 and CXCL10 are pro-inflammatory mediators and that the CXCR3/CXCL10/CXCL9 axis plays a pivotal role in T cell recruitment to the brain in Multiple Sclerosis (MS), little is known about the function of CXCL11 in general and the role it plays in MS in particular.

Whilst reducing the present invention to practice, the present inventors have unexpectedly discovered that CXCL11, unlike its counterpart CXCR3 activators, may act as an anti-inflammatory mediator and accordingly it can be used to as an agent for the treatment of autoimmune disorders.

Figure 2:
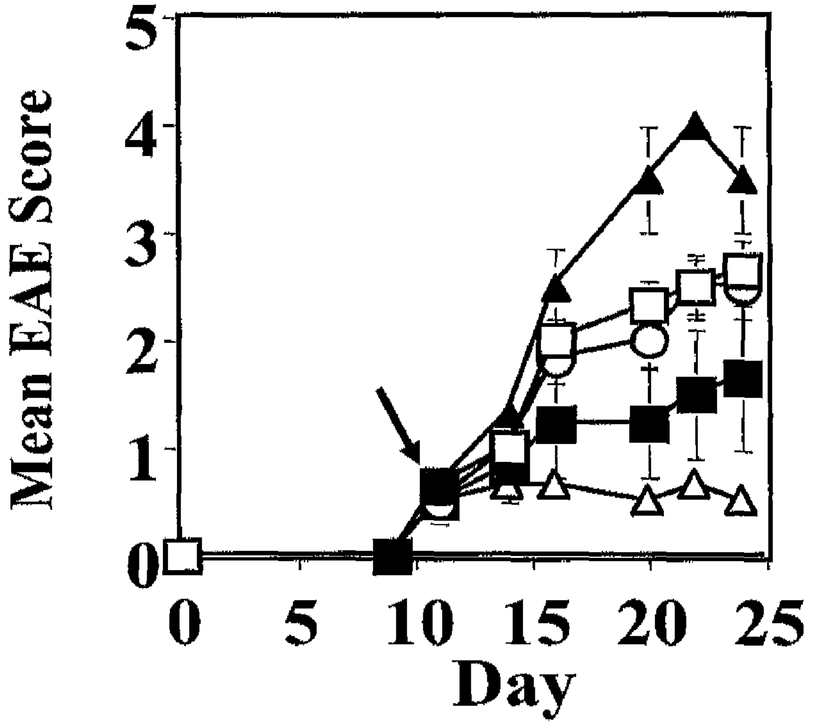
FIG. 2 is a graph depicting the experimental autoimmune encephalomyelitis (EAE) score of mice following administration of anti-CXCL9, anti-CXCL10 or anti-CXCL11 antibodies. The graph shows the results of a representative experiment (1 out of 3 with similar observations) in which, just after the onset of disease (day 11), EAE induced mice were separated into five equally sick groups and administered (on days 11, 13, 15 and 17) either with DNA vaccination based neutralizing antibodies against CXCL9 (close squares), CXCL10 (open triangles) or CXCL11 (close triangles). The remaining two groups of EAE mice were administered with purified antibodies from rats previously injected with an empty vector alone (open circles) or remained untreated (open squares). An observer blind to the experimental protocol then monitored the development and progression of disease. Results are shown as mean maximal score±SE.

Specifically, the present inventors have shown that antibody-mediated blockage of CXCL11 aggravates experimental autoimmune encephalomyelitis (EAE)—an experimentally induced autoimmune disease of the CNS, which serves as an experimental animal model for Multiple sclerosis. This is in sharp contrast to CXCL10 or CXCL9, where neutralization thereof was shown to suppress EAE (FIG. 2).

Figure 4:
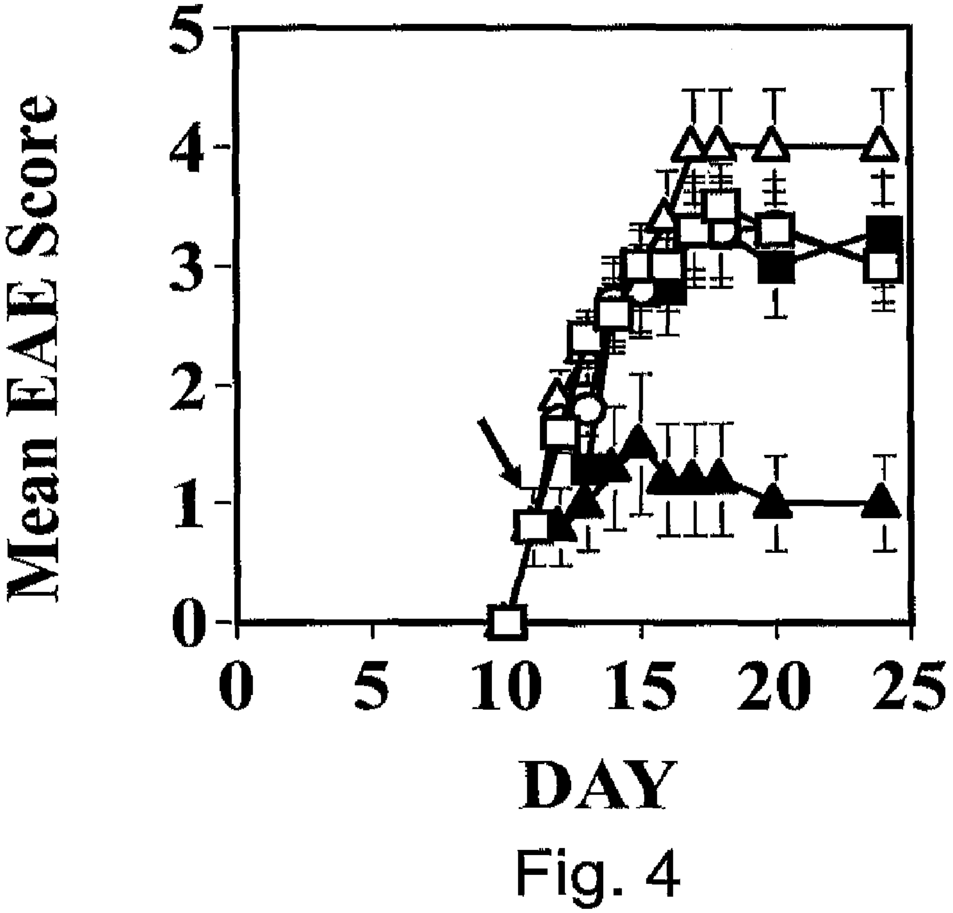
FIG. 4 is a graph depicting the EAE score of mice following administration of the fusion proteins CXCL11-IgG or CXCL10-IgG. The graph shows the results of a representative experiment (1 out of 4 with similar observations) in which, just after the onset of disease (day 11), EAE induced mice were separated into five equally sick groups and administered (on days 11, 13, 15 and 17) with either CXCL10-IgG (open triangles) or CXCL11-IgG (close triangles). The remaining groups were administered with purified β-actin-IgG (close squares), isotype matched IgG1 (open circles), or remained untreated (open squares). An observer blind to the experimental protocol then monitored the development and progression of disease. Results are shown as mean maximal score±SE.

Using a CXCL11-Ig fusion protein, the present inventors tested CXCL11 for its competence to suppress ongoing EAE and showed that it was capable of suppressing disease severity (FIG. 4). In contrast, administration of CXCL10-IgG to EAE induced mice during an ongoing disease significantly aggravated its severity. Successful therapy with CXCL11-IgG led to a significant reduction in secretion of pro-inflammatory mediators TNF-α, IFN-γ and IL-12 (FIGS. 5A-D) and an elevated production of the anti-inflammatory mediators IL-4 and IL-10 (FIGS. 5E-F).

Thus, according to one aspect of the present invention, there is provided a method of treating an autoimmune disease in a subject in need thereof. The method comprises administering to the subject a therapeutically effective amount of CXCL11.

As used herein the term "treating" refers to preventing, curing, reversing, attenuating, alleviating, minimizing, suppressing or halting the deleterious effects of the inflammatory disease.

Herein, the phrase "autoimmune disease" refers to a disease resulting from a disordered immune reaction (e.g., antibody production) generated against components of one's own body (i.e. autoantigens). The immune system of the subject then activates an inflammatory cascade aimed at cells and tissues presenting those specific self antigens. The destruction of the antigen, tissue, cell type, or organ attacked by the individual's own immune system gives rise to the symptoms of the disease.

According to a preferred embodiment of the present invention, the autoimmune disease is Multiple Sclerosis, the inflammatory, demyelinating disease of the central nervous system (CNS) which is typically characterized by various symptoms of neurological dysfunction. Any type of Multiple Sclerosis may be treated according to the teachings of the present invention including relapsing-remitting, secondary progressive, primary progressive, progressive relapsing and special cases of MS with non-standard behavior (also referred to as borderline forms of MS), such as for example without limitation, Neuromyelitis optica (NMO), Balo concentric sclerosis, Schilder disease, Marburg multiple sclerosis, acute disseminated encephalomyelitis (ADEM) and autoimmune variants of peripheral neuropathies. The disease may be treated at any stage.

It will be appreciated that the CXCL11 of the present invention may also be used to treat other inflammatory diseases.

The phrase "inflammatory disease", as used herein, refers to any disease or disorder which includes a component of inflammation, which is imperative to disease onset or progression. The inflammatory disease may be a chronic or a relapsing remitting disease. Other examples of autoimmune and other inflammatory diseases are detailed herein below.

The phrase "subject in need thereof" as used herein, typically refers to a human subject. Typically, the subject has been diagnosed with the inflammatory disease. The subject may or may not have received treatment for the inflammatory disease.

As used herein the term "CXCL11" (also referred to herein as ITAC) refers to at least an active portion of a mammalian (e.g., human) C—X—C chemokine polypeptide having at least one functional property specific to CXCL11 and not to the other CXCR3 ligands (i.e. CXCL9 and CXCL10). Accordingly, the CXCL11 of the present invention may comprise the ability to induce internalization of the CXCR3 receptor, may reduce secretion of pro-inflammatory mediators such as TNF-α, IFN-γ and IL-12 or increase production of anti-inflammatory mediators such as IL-4 and IL-10 from T cells or macrophages. Preferably, the CXCL11 of the present invention comprises all the above functional properties. According to one embodiment, the CXCL11 of the present invention is capable of suppressing on-going MS as illustrated in FIG. 4 (see the Examples section which follows). Examples of CXCL11 amino acid sequences are set forth in GenBank Accession Nos. AAH05292 or EAX05774. Any CXCL11 known in the art can be used in accordance with the teachings of the present invention. For example, recombinant human CXCL11 is available from ProSpec-Tany TechnoGene Ltd, Catalog No. CHM-334, from Cell Sciences and from Biovision.

According to a particularly preferred embodiment of the present invention, CXCL11 is attached to a heterologous amino acid sequence.

As used herein the phrase "heterologous amino acid sequence" refers to an amino acid sequence which does not endogenously form a part of the CXCL11 amino acid sequence. Preferably, the heterologous amino acid sequence does not down-regulate the biological activity (e.g. anti-MS activity) of the CXCL11 polypeptide.

The heterologous amino acid sequence may thus serve to ensure stability of the CXCL11 of the present invention without compromising its activity. For example, the heterologous polypeptide may increase the half-life of the CXCL11 chimeric molecule in the serum. Alternatively, the heterologous amino acid sequence may aid in the isolation of a recombinant CXCL11 as further described herein below. Examples of heterologous amino acid sequences that may be used in accordance with the teachings of the present invention include, but are not limited to, immunoglobulin, galactosidase, glucuronidase, glutathione-S-transferase (GST), carboxy terminal peptide (CTP) from chorionic gonadotrophin (CGβ) and chloramphenicol acetyltransferase (CAT) [see for example Suzuki et al., supra; and U.S. Publication No. 20030171551].

The exact site at which fusion (conjugation) between the heterologous amino acid sequence and the CXCL11 amino acid sequence is not critical. Generally the heterologous amino acid sequence is localized at the amino- or carboxyl-terminus (n-ter or c-ter, respectively) of the CXCL11 polypeptide of the present invention. Particular sites are well known in the art and may be selected in order to optimize the biological activity, secretion or binding characteristics of the chimeric molecules of this aspect of the present invention.

The heterologous amino acid sequence may be attached to the CXCL11 amino acid sequence by any of peptide or non-peptide bond. Attachment of the CXCL11 amino acid sequence to the heterologous amino acid sequence may be effected by direct covalent bonding (peptide bond or a substituted peptide bond) or indirect binding such as by the use of a linker having functional groups. Functional groups include, without limitation, a free carboxylic acid (C(═O)OH), a free amino group ($NH_2$), an ester group (C(═O)OR, where R is alkyl, cycloalkyl or aryl), an acyl halide group (C(═O)A, where A is fluoride, chloride, bromide or iodide), a halide (fluoride, chloride, bromide or iodide), a hydroxyl group (OH), a thiol group (SH), a nitrile group (C≡N), a free C-carbamic group (NR"—C(═O)—OR', where each of R' and R" is independently hydrogen, alkyl, cycloalkyl or aryl).

An example of a heterologous amino acid sequence which may be used in accordance with this aspect of the present invention is an immunoglobulin amino acid sequence, such as the hinge and Fc regions of an immunoglobulin heavy domain (see U.S. Pat. No. 6,777,196). The immunoglobulin moiety in the chimeras of this aspect of the present invention may be obtained from IgG1, IgG2, IgG3 or IgG4 subtypes, IgA, IgE, IgD or IgM, as further discussed hereinbelow. An exemplary human CXCL11 polypeptide linked to an IgG1 moiety is set forth in SEQ ID NO: 6.

Chimeras constructed from a receptor sequence linked to an appropriate immunoglobulin constant domain sequence (immunoadhesins) are known in the art. Immunoadhesins reported in the literature include fusions of the T cell receptor [Gascoigne et al., Proc. Natl. Acad. Sci. USA, 84: 2936-2940 (1987)]; CD4 [Capon et al., Nature 337: 525-531 (1989); Traunecker et al., Nature, 339: 68-70 (1989); Zettmeissl et al., DNA Cell Biol. USA, 9: 347-353 (1990); Byrn et al., Nature, 344: 667-670 (1990)]; L-selectin (homing receptor) [(Watson et al., 3. Cell. Biol., 110:2221-2229 (1990); Watson et al., Nature, 349: 164-167 (1991)]; CD44 [Aruffo et al., Cell, 61: 1303-1313 (1990)]; CD28 and B7 (Linsley et al., J. Exp. Med., 173: 721-730(1991)]; CTLA-4 [Lisley et al., J. Exp. Med. 174: 561-569 (1991)]; CD22 [Stamenkovic et al., Cell, 66:1133-1144 (1991)]; TNF receptor [Ashkenazi et al., Proc. Natl. Acad. Sci. USA, 88: 10535-10539 (1991); Lesslauer et al., Eur. J. Immunol., 27: 2883-2886 (1991); Peppel et al., J. Exp. Med., 174:1483-1489 (1991)]; NP receptors [Bennett et al., J. Biol. Chem. 266:23060-23067 (1991)]; and IgE receptor α [Ridgway et al., J. Cell. Biol., 115: abstr. 1448 (1991)].

Typically, in such fusions the chimeric molecule will retain at least functionally active hinge and CH2 and CH3 domains of the constant region of an immunoglobulin heavy chain. Fusions can also be generated to the C-terminus of the Fc portion of a constant domain, or immediately N-terminal to the CH1 of the heavy chain or the corresponding region of the light chain.

Though it may be possible to conjugate the entire heavy chain constant region to the CXCL11 amino acid sequence of the present invention, it is preferable to fuse shorter sequences. For example, a sequence beginning at the hinge region upstream of the papain cleavage site, which defines IgG Fe chemically; residue 216, taking the first residue of heavy chain constant region to be 114, or analogous sites of other immunoglobulins, may be used in the fusion. In a particularly preferred embodiment, the CXCL11 amino acid sequence is fused to the hinge region and CH2 and CH3, or to the CH1, hinge, CH2 and CH3 domains of an IgG1, IgG2, or IgG3 heavy chain (see U.S. Pat. No. 6,777,196).

As mentioned, the immunoglobulin sequences used in the construction of the chimeric molecules of this aspect of the present invention may be from an IgG immunoglobulin heavy chain constant domain. According to one embodiment of the present invention, the IgG immunoglobulin sequence is for example as set forth in SEQ ID NOs. 3 and 21. Such IgG immunoglobulin sequence can be purified efficiently on immobilized protein A. Selection of a fusion partner may also take into account structural and functional properties of immunoglobulins. Thus, for example, the heterologous peptide may be IgG3 hinge which is longer and more flexible, so it can accommodate larger CXCL11 amino acid sequences that may not fold or function properly when fused to IgG1. Another consideration may be valency; IgG are bivalent homodimers, whereas Ig subtypes like IgA and IgM may give rise to dimeric or pentameric structures, respectively, of the basic Ig homodimer unit. Other considerations in selecting the immunoglobulin portion of the chimeric molecules of this aspect of the present invention are described in U.S. Pat. No. 6,77,196.

The CXCL11 fusion polypeptides of the present invention can be generated using recombinant techniques such as described by Bitter et al. (1987) Methods in Enzymol. 153: 516-544; Studier et al. (1990) Methods in Enzymol. 185:60-89; Brisson et al. (1984) Nature 310:511-514; Takamatsu et al. (1987) EMBO J. 6:307-311; Coruzzi et al. (1984) EMBO J. 3:1671-1680; Brogli et al. (1984) Science 224:838-843; Gurley et al. (1986) Mol. Cell. Biol. 6:559-565 and Weissbach & Weissbach, 1988, Methods for Plant Molecular Biology, Academic Press, NY, Section VIII, pp 421-463.

The heterologous peptides may also be chemically linked to CXCL11 following the independent generation of each. Thus, the two peptides may be covalently or non-covalently linked using any linking or binding method and/or any suitable chemical linker known in the art. Such linkage can be direct or indirect, as by means of a peptide bond or via covalent bonding to an intervening linker element, such as a linker peptide or other chemical moiety, such as an organic polymer. Such chimeric peptides may be linked via bonding at the carboxy (C) or amino (N) termini of the peptides, or via bonding to internal chemical groups such as straight, branched, or cyclic side chains, internal carbon or nitrogen atoms, and the like. The exact type and chemical nature of such cross-linkers and cross linking methods is preferably adapted to the type and nature of the peptides used.

It will be appreciated that treatment of autoimmune diseases according to the present invention may be combined with other treatment methods known in the art (i.e., combination therapy). Thus for example, Multiple Sclerosis may be treated with the CXCL11 of the present invention in conjunction with other agents including but are not limited to, Interferon Beta 1a, Interferon Beta 1b, Glatiramer Acetate, Mitoxantrone, MethylPrednisolone, Prednisone, Prednisolone, Dexamethasone, Adreno-corticotrophic Hormone (ACTH) and Corticotrophin. The present invention therefore contemplates articles of manufacture comprising CXCL11 and an anti-Multiple Sclerosis agent being packaged in a packaging material and identified in print, in or on the packaging material for use in the treatment of Multiple Sclerosis.

As mentioned, the CXCL11 polypeptides of the present invention may be used to treat inflammatory diseases other than Multiple Sclerosis. Such inflammation associated diseases and disorders are summarized infra.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2): 49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S 125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8): 1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann NY Acad Sci.

1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Sac Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann NY Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et at, J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth G S. Ann. Rev. Immunol. 8:647;

Zimmet P. Diabetes Res Clin Pract 1996 October; 34 Suppl: S125), autoimmune thyroid diseases, Graves' disease (Orgiazzi J. Endocrinol Metab Clin North Am 2000. June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12):7262), Hashimoto's thyroiditis (Toyoda N. et at, Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann NY Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann NY Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

CXCL11 of the present invention can be administered to the subject per se, or as part of a pharmaceutical composition, which also includes a physiologically acceptable carrier. The purpose of a pharmaceutical composition is to facilitate administration of the active ingredient to an organism.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

As used herein, the term "active ingredient" refers to the preparation accountable for the intended biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media [Mutter et al. (1979)].

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., a nucleic acid construct) effective to prevent, alleviate, or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

The discovery that CXCL11 polarizes T cells into T regulatory cells which secrete anti-inflammatory cytokines (e.g. IL-10 and IL-4) instead of pro-inflammatory cytokines (e.g., IL-12 and TNF-α), see FIGS. 10A-K, suggests the use of CXCL11 in isolated settings so as to avoid undesired side effects. As depicted in detail in Examples 4 and 6 hereinbelow, treatment of multiple sclerosis (in a murine model) by ex vivo therapy via administration of antigen specific, IL-10 producing T cells selected in the presence of CXCL11-IgG lead to fast remission in active disease.

Thus, according to another aspect of the present invention there is provided a method of treating an autoimmune disease in a subject in need thereof, the method comprising ex vivo contacting T cells with CXCL11 under conditions which result in generation of regulatory T cells and administering the regulatory T cells to the subject, thereby treating the autoimmune disease in the subject.

As used herein the term "ex vivo contacting" refers to the process of isolating T cells from a body and culturing them with CXCL11, as for example in a culture dish or by an automated machine (e.g. cell dialysis apparatus which by automated settings separates cells from body fluids and cultures them with the appropriate substances in a sterile environment), as to enable direct contact of the cells with CXCL11.

Thus, T cells can be isolated from an autologous origin (i.e. from the multiple sclerosis affected subject), from a syngeneic donor, from an allogeneic donor or from a xenogeneic donor. The T cells may also be obtained from a multiple sclerosis affected subject undergoing CXCL11 treatment.

Furthermore, the T cells may be comprised in a crude blood sample, in PBMC, or further purified. In an exemplary embodiment, the isolated T cells are purified CD4+ T cells such as naive CD4+ T cells. To avoid the effects of graft versus host disease (GVHD) exhibited by CD8+ T cells (i.e. cytotoxic T cells), purification of CD4+ T cells, rather than CD8+ T cells is effected.

Several techniques are known in the art for isolating T cells [see for example, Leavitt et al., Hum. Gene Ther. 5: 1115-1120 (1994)]. The expression of surface markers facilitates identification and purification of T cells. Methods of identification and isolation of T cells include FACS, panning with magnetic beads and human T-cell subset columns. Cells isolated according to the teachings of the present invention should stay sterile and preferably maintained out of the body for a minimal time period.

Subsequent to cell isolation, the T cells are subjected to culture in the presence of CXCL11. Such culture conditions are described in detail in Example 7 (in the Example section hereinbelow). For example, the isolated T cells (about 300,000 cell/ml) may be cultured in the presence of rhCXCL11 (10 ng/ml) and a stimulatory peptide (e.g. anti-CD3ϵ mAb and/or anti-CD28 mAb at a concentration of 2 μg/ml), in a humidified 7.5% $CO_2$ atmosphere at 37° C. for 48 hours.

Such culturing conditions enable polarization of the isolated T cells into regulatory T cells. In an exemplary embodiment, such culturing conditions polarize T cells to become IL-10 and/or IL-4 secreting cells. Furthermore, following these culturing conditions, a reduction in secretion of pro-inflammatory cytokines (e.g. IFN-γ) is noted.

As used herein the terms "regulatory T cells" refers to the subset of T cells, also known as suppressor T cells, which are a specialized subpopulation of T cells that act to suppress activation of the immune system and thereby maintain immune system homeostasis and tolerance to self-antigens. CD4+ regulatory T cells may express the membrane markers CD25 and/or Foxp3.

CXCL11 treated regulatory T cells are then administered to the subject (e.g., a subject diagnosed with Multiple Sclerosis as described hereinabove).

Those skilled in the art are capable of determining when and how to administer the T cells to thereby treat Multiple Sclerosis. The administration can be carried out via local injection, by administration into the systemic (e. g., via the blood stream or the peritoneal cavity) or portal circulation system, or by any other practical means (see for example, WO/2001/078752).

According to an embodiment of the present teachings, the regulatory T cells are specifically selected (i.e. isolated from the cell culture) prior to administering to the subject. Methods of isolating regulatory T cells are described hereinabove.

As depicted above, the T cells used for ex vivo therapy according to the present teachings may be from a non-syngeneic source (i.e. from an allogeneic or xenogeneic donor). Although administration of purified regulatory T cells should not cause GVHD, in cases where there is a risk of GVHD or occurrence of GVHD, any GVHD treatment protocol may be employed. Such treatments may include administration of immunosuppressant drugs (e.g., sirolimus, tacrolimus, cyclosporine, CTLA4-Ig, anti-CD40L antibody or rapamycin) which may be administered individually or in combination. Immunosuppressant drugs may be administered prior to, concomitantly with, or following administration of the regulatory T cells.

Furthermore, administering non-syngeneic cells may cause rejection of the cells used for ex vivo therapy. Several approaches have been developed to reduce the likelihood of rejection of these non-syngeneic cells. These include either suppressing the recipient immune system (as described above) or encapsulating the non-autologous T cells in immunoisolating, semipermeable membranes prior to administration.

Encapsulation techniques are generally classified as microencapsulation, involving small spherical vehicles, and macroencapsulation, involving larger flat-sheet and hollow-fiber membranes (Uludag, H. et al. (2000). Technology of mammalian cell encapsulation. Adv Drug Deliv Rev 42, 29-64).

Methods of preparing microcapsules are known in the art and include for example those disclosed in: Lu, M. Z. et al. (2000). Cell encapsulation with alginate and alpha-phenoxycinnamylidene-acetylated poly(allylamine). Biotechnol Bioeng 70, 479-483; Chang, T. M. and Prakash, S. (2001) Procedures for microencapsulation of enzymes, cells and genetically engineered microorganisms. Mol Biotechnol 17, 249-260; and Lu, M. Z., et al. (2000). A novel cell encapsulation method using photosensitive poly(allylamine alpha-cyanocinnamylideneacetate). J Microencapsul 17, 245-521.

For example, microcapsules are prepared using modified collagen in a complex with a ter-polymer shell of 2-hydroxyethyl methylacrylate (HEMA), methacrylic acid (MAA), and methyl methacrylate (MMA), resulting in a capsule thickness of 2-5 μm. Such microcapsules can be further encapsulated with an additional 2-5 μm of ter-polymer shells in order to impart a negatively charged smooth surface and to minimize plasma protein absorption (Chia, S. M. et al. (2002). Multi-layered microcapsules for cell encapsulation. Biomaterials 23, 849-856).

Other microcapsules are based on alginate, a marine polysaccharide (Sambanis, A. (2003). Encapsulated islets in diabetes treatment. Diabetes Thechnol Ther 5, 665-668), or its derivatives. For example, microcapsules can be prepared by the polyelectrolyte complexation between the polyanions sodium alginate and sodium cellulose sulphate and the polycation poly(methylene-co-guanidine) hydrochloride in the presence of calcium chloride.

It will be appreciated that cell encapsulation is improved when smaller capsules are used. Thus, for instance, the quality control, mechanical stability, diffusion properties, and in vitro activities of encapsulated cells improved when the capsule size was reduced from 1 mm to 400 μm (Canaple, L. et al. (2002). Improving cell encapsulation through size control. J Biomater Sci Polym Ed 13, 783-96). Moreover, nanoporous biocapsules with well-controlled pore size as small as 7 nm, tailored surface chemistries, and precise microarchitectures were found to successfully immunoisolate microenvironments for cells (See: Williams, D. (1999). Small is beautiful: microparticle and nanoparticle technology in medical devices. Med Device Technol 10, 6-9; and Desai, T. A. (2002). Microfabrication technology for pancreatic cell encapsulation. Expert Opin Biol Ther 2, 633-646).

Treatment of an autoimmune disease, such as multiple sclerosis, according to the present teachings may be repeated as required, such as during relapse.

Thus, the present invention provides compositions and methods of treating MS using in vivo and ex-vivo settings.

As used herein the term “about” refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, “Molecular Cloning: A laboratory Manual” Sambrook et al., (1989); “Current Protocols in Molecular Biology” Volumes I-III Ausubel, R. M., ed. (1994); Ausubel et al., “Current Protocols in Molecular Biology”, John Wiley and Sons, Baltimore, Md. (1989); Perbal, “A Practical Guide to Molecular Cloning”, John Wiley & Sons, New York (1988); Watson et al., “Recombinant DNA”, Scientific American Books, New York; Birren et al. (eds) “Genome Analysis: A Laboratory Manual Series”, Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; “Cell Biology: A Laboratory Handbook”, Volumes I-III Cellis, J. E., ed. (1994); “Culture of Animal Cells—A Manual of Basic Technique” by Freshney, Wiley-Liss, N.Y. (1994), Third Edition; “Current Protocols in Immunology” Volumes I-III Coligan J. E., ed. (1994); Stites et al. (eds), “Basic and Clinical Immunology” (8th Edition), Appleton & Lange, Norwalk, Conn. (1994); Mishell and Shiigi (eds), “Selected Methods in Cellular Immunology”, W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; “Oligonucleotide Synthesis” Gait, M. J., ed. (1984); “Nucleic Acid Hybridization” Hames, B. D., and Higgins S. J., eds. (1985); “Transcription and Translation” Hames, B. D., and Higgins S. J., eds. (1984); “Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Neutralizing CXCL10 and CXCL9 Suppresses Experimental Autoimmune Encephalomyelitis (EAE) While Neutralizing CXCL11 Aggravates its Manifestation In order to elucidate the role of the different CXCR3 ligands (CXCL9, CXCL10 and CXCL11) in the regulation of Multiple Sclerosis, antibodies generated against each of the three CXCR3 ligands were produced and administered to mice during experimental autoimmune encephalomyelitis (EAE)—an experimentally induced autoimmune disease of the CNS, which serves as an experimental animal model for multiple sclerosis.

Materials and Methods

Animals 6-week-old female C57BL/6 mice were purchased from Harlan (Jerusalem, Israel) and maintained under specific pathogen-free conditions.

Peptide Antigens

Myelin oligodendrocyte glycoprotein $MOG_{35-55}$ (SEQ ID NO: 31) was constructed by the PAN facility of the Beckman Center of Stanford University. After purification by HPLC, the sequence was confirmed by amino acid analysis and the mass was checked by mass spectroscopy. Purification of the peptide used in this invention was >95%.

Induction of Active EAE

Active induction of EAE was induced by immunizing C57BL\6 female mice with $MOGp_{35-55}$/CFA as previously described by Tompkins et al. [Tompkins et al., J Immunol (2002) 168:4173-83]. Mice were monitored daily for clinical signs by an observer blind to the treatment protocol. EAE was scored as follows: 0—clinically normal; 1—flaccid tail; 2—hind limb paralysis; 3—total hind limb paralysis, accompanied by an apparent front limb paralysis; 4—total hind limb and front limb paralysis; and 5—death.

Generation of Anti-CXCL9, Anti-CXCL10 and Anti-CXCL11 Neutralizing Antibodies

Polyclonal antibodies (Abs) to CXCL9, CXCL10 and CXCL11 were generated as was previously described [Goldberg et al., J Immunol (2004) 173:6465-6471]. Briefly, female Lewis rats were subjected to subsequent administrations (in two week intervals) of murine CXCL9, CXCL10 or CXCL11 encoding DNA plasmids as was previously described [Wildbaum et al., J Immunol (2002) 168:5885-92]. Ten days after the last administration, rats were injected with 100 μg commercial recombinant gene product encoded by each vaccine (R&D Systems, Minneapolis, Minn.) emulsified in IFA (Incomplete Freud's Adjuvant). Ten days later, anti-CXCL9, anti-CXCL10 or anti-CXCL11 antibodies were purified from sera of these rats by a two step purification: (1) IgG fraction was purified using a High-Trap Protein G column (BD Biosciences, Piscataway, N.J.) and (2) cytokine-specific Abs were purified using a cyanogen bromide-activated Sepharose column, as described hereinafter. Each recombinant mouse cytokine (at a concentration of 5 mg), was bound to cyanogen bromide-activated Sepharose column according to the manufacturer's instructions (Pharmacia Biotech, Uppsala, Sweden). Each IgG fraction was loaded on the column and then eluted by an acidic elution buffer (glycine, pH 2.5). Isotype determination of the purified Abs revealed that purified Abs were mostly of the IgG2a isotype (data not shown).

Administration of Anti-CXCL9, Anti-CXCL10 and Anti-CXCL11 Neutralizing Antibodies to Mice Just after disease onset (day 11), EAE induced mice were separated into five groups based on the severity of the disease (6 per group). Three of these groups were subjected to intramuscular (i.m.) injections of one of the antibodies (against CXCL9, CXCL10 or CXCL11) or control antibodies from rats previously administered with an empty vector. All antibodies were administered from day 11-on every other day. One group of mice remained untreated. An observer blind to the experimental protocol then monitored the development and progression of disease.

Migration Assay

Cell migration assay was performed. CXCR3+ T cells from a MOGp33-55 specific encephalitogenic CD4+ T cell line were loaded in the upper chamber of a 6.5-mm diameter, 5-μm-pore polycarbonate Transwell cultureinsert (Costar, Cambridge, Mass.). The lower chamber contained each detected chemokine, or chemokine based Ig fusion protein, with, or without the addition of chemokine specific neutralizing antibodies. Incubation of cells was carried out at 37° C. in 7.5% $CO_2$ for 2 hours. Migrated cells were collected and counted using a FACSCalibur (BD Biosciences). Percentage of cell migration was calculated as the number of cells that migrated to lower chamber divided by number of cells originally plated in the upper chamber.

Results

Figure 1A:
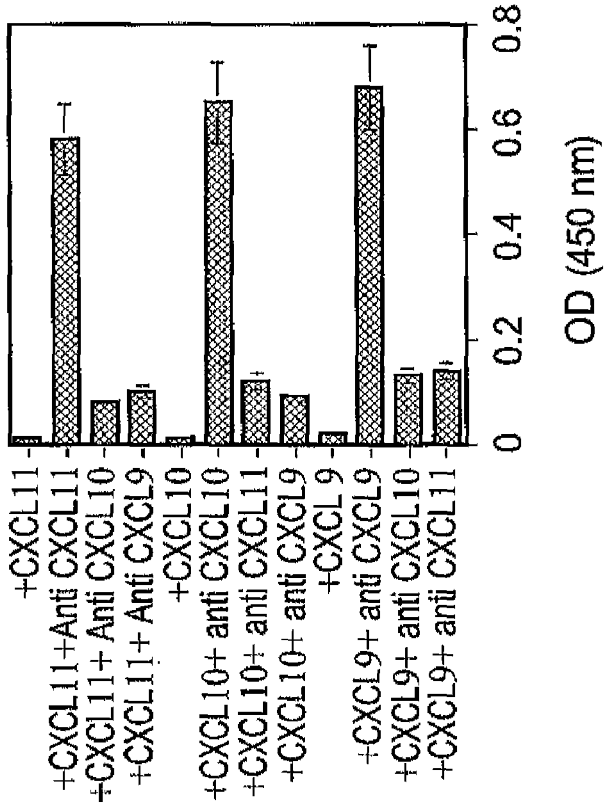
FIGS. 1A-B are bar graphs depicting specificity of anti-CXCL9, anti-CXCL10 and anti-CXCL11 antibodies.
Figure 1B:
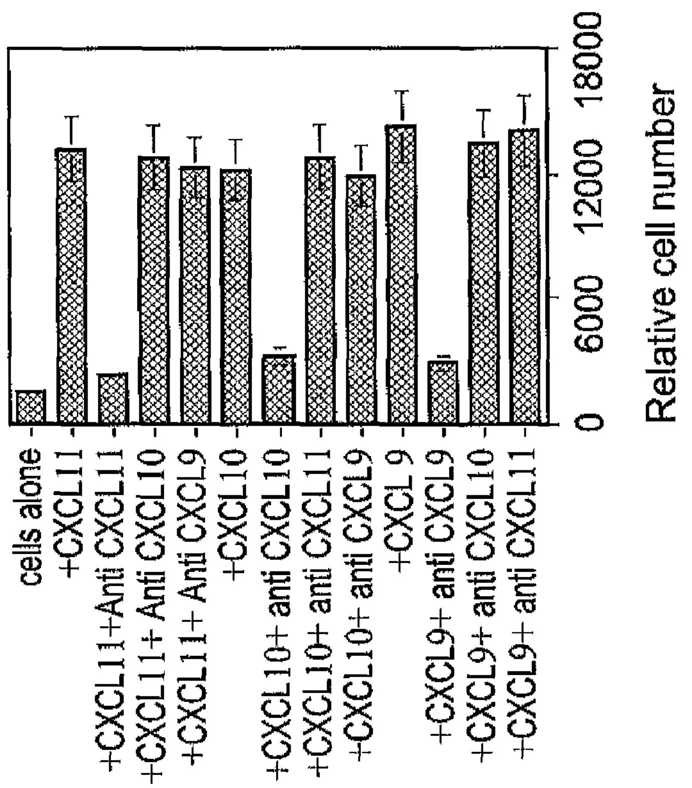

Antibodies generated against each of the three CXCR3 ligands (CXCL9, CXCL10 and CXCL11) were first determined for their specificity. As shown in FIG. 1A, each antibody selectively bound its recombinant target gene product, but not each of the other CXCR3 ligands. Moreover, these antibodies did not bind numerous other chemokines that have been associated with regulation of inflammatory responses including: CCL2, CCL5 and CXCL12 (data not shown). Trans-well migration analysis was then carried out to verify antibody neutralization of the chemokines. FIG. 1B shows that indeed each antibody selectively blocked chemokine-induced migration of its target chemokine (about 80% each, $p<0.001$), but not migration induced by the other CXCR3 ligands.

Subjection of EAE induced mice to CXCL9, CXCL10 or CXCL11 antibodies differentially affected the severity of an ongoing disease as shown in FIG. 2. Neutralization of CXCL10 significantly suppressed the disease (mean maximal score of 0.66±0.23 compared to 2.83±0.66 for control mice, $p<0.001$) while neutralization of CXCL9 also suppressed the disease (mean maximal score of 1.66±0.35 compared to 2.83±0.66 for control mice, $p<0.03$), but significantly less than the effect of anti CXCL10 therapy ($p<0.03$). In sharp contrast, administration of anti-CXCL11 antibodies aggravated the severity of the disease (mean maximal score of 4±0 compared to 2.83±0.66 for control mice, $p<0.001$), suggesting that while CXCL9 and CXCL10 function as pro-inflammatory cytokines, CXCL11 functions as a regulatory chemokine that antagonizes the pro-inflammatory activities of the other two CXCR3 ligands.

Example 2

Construction of CXCL11-Ig and CXCL10-Ig Fusion Proteins Which Maintain Their Functional Properties Chemokines have a very short half life. Therefore, in an attempt to study the potential therapeutic competence of CXCL11, in comparison to CXCL10, recombinant fusion molecules comprising CXCL11 or CXCL10 fused to the IgG1 heavy chain Fc were generated which maintained their functional properties.

Materials and Methods

Construction of CXCL11 IgG and CXCL10-IgG Fusion Proteins

The nucleic acid vectors encoding CXCL11-Ig or CXCL10-Ig fusion proteins of the present invention were constructed as follows: cDNA encoding the constant region (Hinge-CH2-CH3, SEQ ID NO: 3) of human IgG1 heavy chain was generated by RT-PCR of RNA extracted from LPS and IL-4 activated peripheral blood mononuclear cells (PBMC) using the primers: sense, 5' ctcgagCCCAAATCTTGTGACAAAAC 3' (SEQ ID NO: 7) and antisense: 5' gggcccTTTACCCGGGGACAGGGAGA 3' (SEQ ID NO: 8). cDNA encoding the constant region (Hinge-CH2-CH3, SEQ ID NO: 21) of murine IgG1 heavy chain was generated by RT-PCR of RNA extracted from LPS and IL-4 activated mouse spleen cells using the primers: sense, 5' CCGCTCGAGGTGCCCAGGGATTGTGGTTG 3' (SEQ ID NO: 23) and antisense: 5' TTGTTCGGGCCCTTTACCAGGAGAGTGGGAGA 3' (SEQ ID NO: 24). PCR products were digested with XhoI and ApaI and ligated into mammalian expression/secretion vector pSecTag2/Hygro B (Invitrogen Life Technologies, San Diego, Calif.).

cDNA encoding mouse CXCL11 (GenBank Accession No. NM_019494, SEQ ID NO: 9 was generated by RT-PCR of RNA extracted from mouse splenocytes using the primers: sense, 5' gctagcATGAACAGGAAGGTCACAGCCATAGC 3' (SEQ ID NO: 11) and antisense, 5' ctcgagCATGTTTTGACGCCTTAAAAAATT 3' (SEQ ID NO: 12). cDNA encoding mouse CXCL10 (GenBank Accession No. NM_NM_021274 SEQ ID NO: 15) was generated by RT-PCR of RNA extracted from mouse splenocytes using the primers: sense, 5' gctagcATGAACCCAAGTGCTGCCGTCATTTT 3' (SEQ ID NO: 17) and antisense, 5' ctcgagAGGAGCCCTTTTAGACCTTTTTTG 3' (SEQ ID NO: 18). cDNA encoding β-actin (SEQ ID NO: 25), used as a control, was generated by RT-PCR of RNA extracted from mouse splenocytes using the primers: sense, 5' gctagc ATGGATGACGATATCGCTGCGCTGGTCGT 3' (SEQ ID NO: 27) and antisense, 5' ctcgag GAAGCACTTGCGGTGCACGATGGAG 3' (SEQ ID NO: 28). PCR products were digested with NheI and XhoI and following sequence verification, the amplified PCR products were subcloned into the pSec-Tag2 vector (Invitrogen, San Diego, Calif.) upstream of the mouse IgG1 fragments to create the fusion proteins: CXCL11-Ig (SEQ ID NO: 14), CXCL10-Ig (SEQ ID NO: 29) or the control peptide β-actin-Ig (SEQ ID NO: 30).

Since alterations in the amino acid sequence at the N-terminus of chemokines might change their properties, NheI was selected for the cloning procedure and the original murine kappa chain leader sequence found in pSecTag2/Hygro B was replaced by either mouse CXCL11-IgG leader sequence, CXCL10-IgG leader sequence, or β-actin-IgG leader sequence accordingly. The fused fragments were sequenced by dideoxynucleotide sequencing (Sequenase version 2; Upstate Biotechnology, Cleveland, Ohio).

Expression and Purification of CXCL11-IgG and CXCL10-IgG Fusion Proteins

The pSec-CXCL11-IgG, pSec-CXCL10-IgG or pSec-β-actin-IgG plasmids were separately co-transfected into DG44 Chinese hamster ovary (CHO) cells that have a double deletion for the dihydrofolate reductase (DHFR) gene (DG44 CHO DHFR$^{-/-}$ cells, provided by Dr. Lawrence Chasin from Columbia University, USA, ATCC Accession No. CRL-9096), with CHO DHFR minigene vector, which transfects DHFR-deficient CHO cells with high efficiency, using jet PEI (Polypluse transfection—Illkirch Cedex, France) according the manufacturer's protocol. Stably transfected cells were selected in a culture medium (MEM-alpha) containing hygromycine (200 μg/ml) and increasing doses of methotrixate (2.5 nM to 0.1 mM). The fusion protein was expressed as a disulphide-linked homodimer similar to IgG1, and it had a molecular weight of approximately 72 kDa consisting of two identical 36 kDa subunits. The fusion protein was purified from the culture medium by High-Trap protein G affinity column (BD Biosciences, Piscataway, N.J.) and verified by Western blot analysis using mouse anti-hIg (Jackson ImmunoResearch Laboratories, West Grove, Pa.) as primary antibody and donkey anti-mouse HRP-conjugated antibody (Jackson ImmunoResearch Laboratories, West Grove, Pa.) as secondary antibody.

Results

Figure 3:
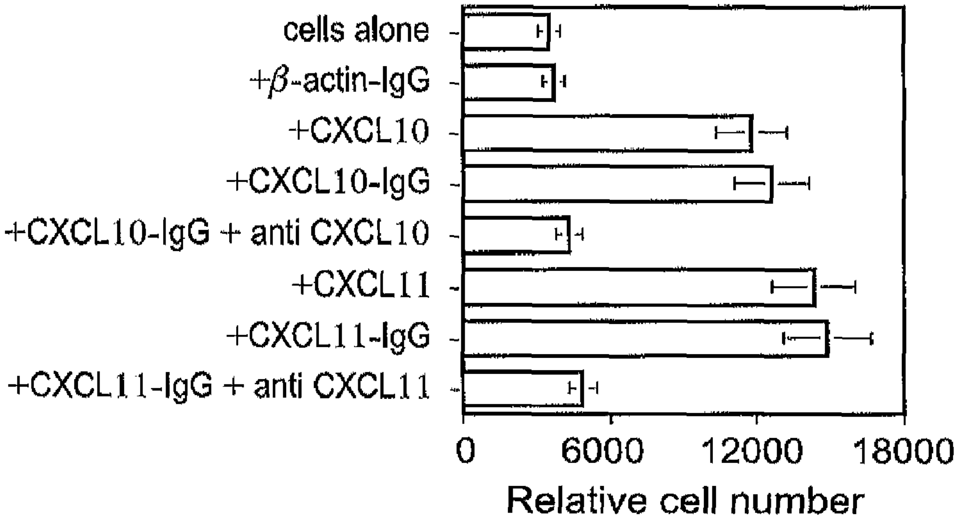
FIG. 3 is a graph depicting CXCL11-IgG and CXCL10-IgG fusion proteins preserving their functional properties. The graph shows the ability of CXCL11-IgG and CXCL10-IgG fusion proteins to attract CXCR3+ T cells in a trans-well system and the competence of anti CXCL11 and anti CXCL10 neutralizing antibodies (R&D Systems) to selectively inhibit the chemokine-induced migration of each chemokine. Results of triplicate measurements were analyzed by flow cytometry and are shown as mean relative cell number±SE.

Recombinant CXCL11-IgG and CXCL10-IgG fusion proteins were successfully generated, each preserving its selective target recognition pattern and its ability to attract CXCR3+ T cells in a trans-well system (FIG. 3). The chemokine specific neutralizing antibodies generated according to the teachings of the present invention (see Example 1), as well as commercially available neutralizing antibodies (data not shown) could selectively neutralize the ability of each fusion protein to attract CXCR3+ T cells (FIG. 3).

Preliminary experiments (data not shown) showed that the fusion proteins constructed with human IgG1 (Fe) or the mouse IgG1 (Fe) exerted the same biological properties, as illustrated in FIG. 3. Since the in vivo experimental studies included interventions in a long-term form of ongoing EAE, inventors used the murine constructs encoding mouse IgG1.

Example 3

CXCL11-Ig Fusion Protein Suppresses Ongoing EAE by Selecting IL-10 and IL-4 Producing T Cells Since anti-CXCL11 antibodies were shown to aggravate the severity of EAE, the present inventors hypothesized that CXCL11 antagonizes CXCL10. In order to test this hypothesis a CXCL11-Ig fusion protein was tested for its competence to suppress ongoing EAE.

Materials and Methods

Animals

Mice were used as described in detail in Example 1 hereinabove.

Induction of Active Disease

Induction of active EAE was effected as described in detail in Example 1 hereinabove.

Generation of CXCL11-hIg and CXCL10-hIg Fusion Proteins

As described in detail in Example 2, hereinabove.

Administration of CXCL11-Ig and CXCL10-Ig Fusion Proteins to EAE Induced Mice

Just after the onset of active EAE disease (day 11), C57BL\6 female mice were separated into five groups of equally sick mice (6 per group). On days 11, 13, 15, and 17 after the induction of disease, EAE mice were subjected to i.m. injections of either CXCL10-IgG or CXCL11-IgG at a concentration of 200 μg/mouse. The remaining three groups were administered with either isotype-matched control IgG, purified β-actin-IgG or remained untreated. An observer blind to the experimental protocol then monitored the development and progression of disease.

Isolation and ex-vivo Activation of EAE Primary T Cells

Spleen cells were collected from the cervical lymph nodes (CLN) of mice at the peak of disease (18 days post induction of EAE). Cells were cultured in a humidified 7.5% $CO_2$ atmosphere at 37° C. and stimulated with 50 μg/ml $MOG_{35-53}$ peptide (target antigen). $10\times10^6$ spleen cells were cultured in 24-well plates in the presence of CXCL10-IgG, CXCL11-IgG or PBS for 72 hours. Supernatants were collected and analyzed by ELISA.

ELISA

Secreted levels of IL-10, IL-12, TNF-α, IFNγ, IL-2 and IL-4 were each measured by commercially available ELISA kits: IL-10, IL-2 and IFN-γ (BioLegend, San Diego, Calif.), IL-12 and TNF-α (Bender Medical Systems, Vienna, Austria), and IL-4 (BioLegend, San Diego, Calif.).

Results

As shown in FIG. 4, treatment of EAE induced mice with CXCL11-IgG rapidly suppressed disease severity (On day 20, mean EAE score of treated mice was 0.83±0.33 compared to 3±0.66 in control mice, p<0.001). By contrast, administration of CXCL10-IgG to EAE induced mice during an ongoing disease significantly aggravated its severity (On day 20, mean EAE score of CXCL10-IgG treated mice was 4±0.5 compared to 3±0.66 in control mice, p<0.01). Subjection of EAE induced mice to the control fusion protein (β-actin-IgG) had no effect on the manifestation of the disease (FIG. 4).

Figure 5A:
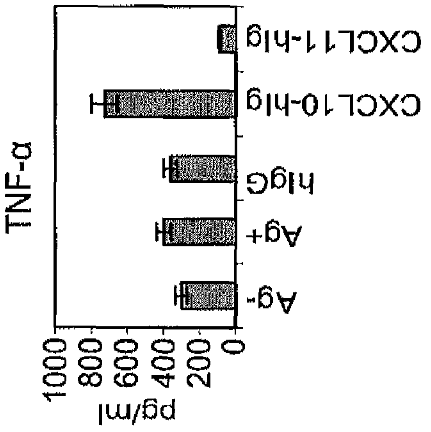
FIGS. 5A-F are bar graphs depicting ex-vivo production of cytokines in primary T cell cultures in response to the target antigen ($MOG_{35-55}$) Primary T cells were collected from the cervical lymph nodes (CLN) of EAE induced mice at the peak of disease (on day 15). T cells were stimulated with the target antigen $MOG_{35-53}$ peptide and were cultured in the presence of CXCL10-IgG, CXCL11-IgG or PBS or hIgG control antibody for 72 hours. Supernatants were collected and analyzed by ELISA.
Figure 5B:
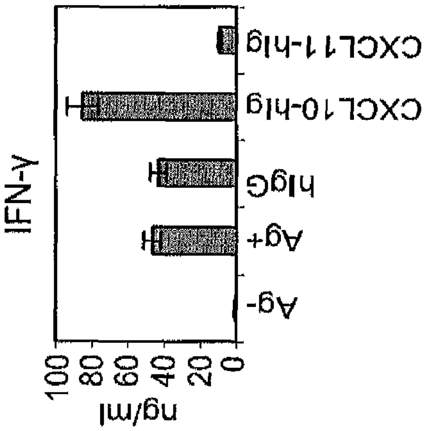
Figure 5C:
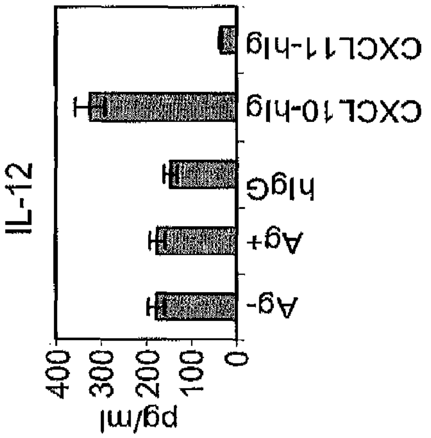
Figure 5D:
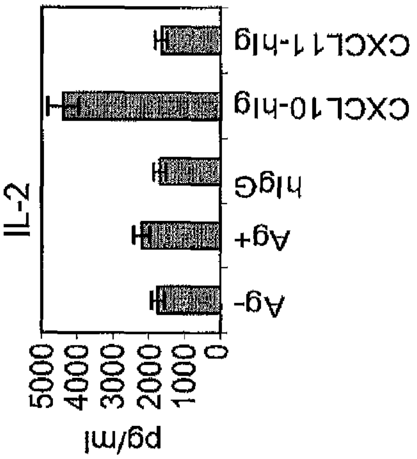
Figure 5E:
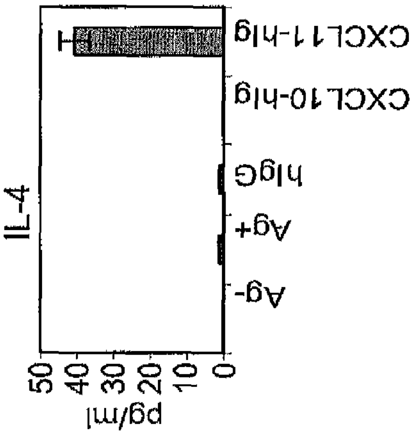
Figure 5F:
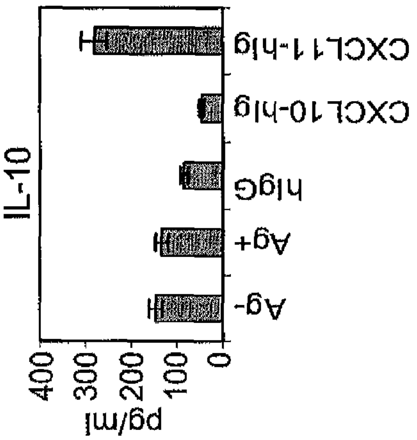

Results clearly showed that treatment of EAE induced mice with CXCL10-IgG lead to a significant elevation in TNF-α secretion from primary T cells (FIG. 5A, 728±63 compared to 401±38 pg/ml for target antigen, p<0.001). Similar results were reported for IFN-γ secretion (FIG. 5B, 86.5±6.3 compared to 46±4.6 ng/ml for target antigen, p<0.01), IL-12 secretion (FIG. 5C, 325±38 compared to 176±62 pg/ml for target antigen, p<0.01) and IL-2 secretion (FIG. 5D, 4400±460 compared to 2200±300 pg/ml for target antigen). In sharp contrast, successful therapy with CXCL11-IgG lead to a significant reduction in TNF-α secretion (FIG. 5A, 90±12 compared to 401±38 pg/ml for target antigen, p<0.0001), IFN-γ secretion (FIG. 5B, 9±2 compared to 46±4.6 ng/ml for target antigen, p<0.0001), and IL-12 secretion (FIG. 5C, 36±4 compared to 176±62 pg/ml for target antigen, p<0.0001). Additionally, CXCL11-IgG treatment led to an elevated production of the immunoregulatory cytokines IL-4 (FIG. 5E, 1±0.5 compared to 41±6 pg/ml, p<0.0001) and IL-10 (FIG. 5F, 280±33 compared to 133±16 pg/ml for target antigen, p<0.001).

Example 4

Antigen-Specific T Cells from Protected Donors Suppress Active EAE in Adoptive Transfer Experiments In an attempt to elucidate whether CXCL11 selects antigen specific regulatory T cells (T-reg), T cells from EAE induced donor mice treated with CXCL11-IgG, were selectively transferred to EAE induced recipient mice.

Materials and Methods

Animals

Mice were used as described in detail in Example 1 hereinabove.

Induction of Active Disease

Induction of active EAE was effected as described in detail in Example 1 hereinabove.

Generation of CXCL11-hIg Fusion Protein

As described in detail in Example 2, hereinabove.

Administration of CXCL11-Ig Fusion Protein to EAE Induced Mice

As described in detail in Example 3, hereinabove.

Generation of Spleen Cells from Donor Mice and Adoptive Transfer to Recipient EAE Induced Mice Primary spleen cells from CXCL11-IgG treated or untreated EAE induced donor mice were collected from mice 15 days post induction of EAE. Cells were cultured in a humidified 7.5% $CO_2$ atmosphere at 37° C. and stimulated with their target autoimmune antigen, $MOG_{35-53}$ peptide, at a concentration of 50 μg/ml for 3 days. These cells were then administered ($30\times10^6$/mouse) to EAE induced recipient mice, just after the onset of disease (on day 11).

Results

Figure 6:
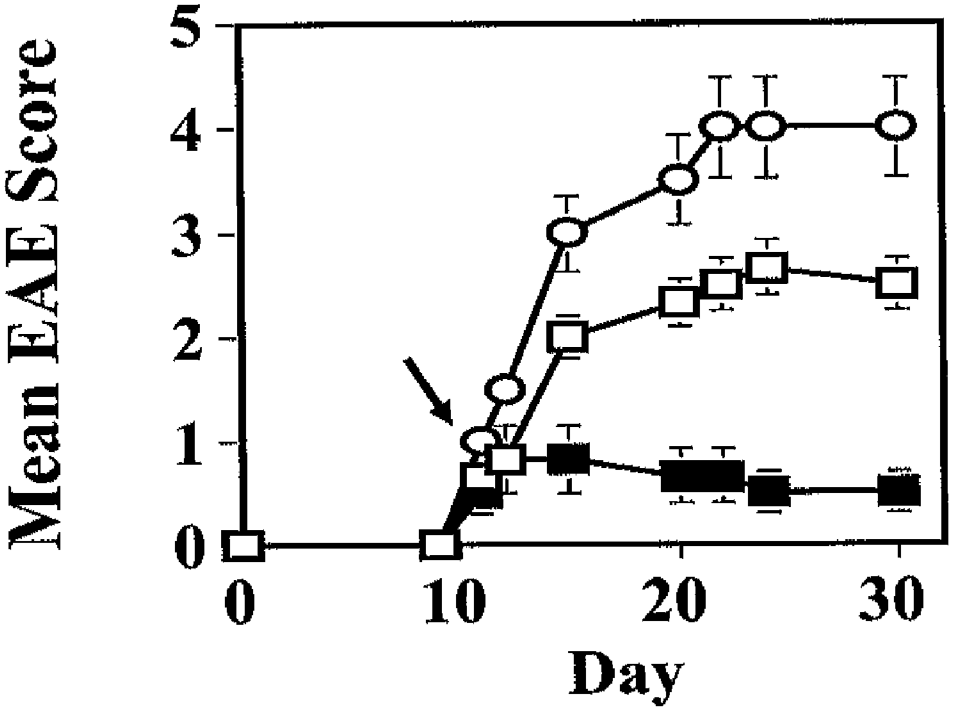
FIG. 6 is a graph depicting the EAE score of mice following transfer of T cells from EAE treated or untreated donors. Primary spleen cells from CXCL11-IgG treated or untreated EAE induced donor mice were cultured with their $MOG_{35-55}$ target antigen and transferred to EAE induced recipient mice, just after the onset of disease as follows: cells from donors treated with CXCL11IgG (close squares); cells from control EAE induced mice (open circles); and mice not subjected to donor T cells (open squares). An observer blind to the experimental protocol then monitored the development and progression of disease. Results presented are representative results of one out of two experiments with very similar observations Results are shown as mean maximal score of six mice per group±SE.

As evident from the results (FIG. 6), administration of T cells from CXCL11-IgG treated donor mice to EAE induced recipient mice lead to a fast remission of active EAE disease (on day 25, mean EAE score recorded was 0.5±0.3 compared to 2.66±0.3 for control mice, p<0.001). Conversely, administration of T cells from untreated EAE induced mice during ongoing disease significantly aggravated its severity (On day 25, mean EAE score recorded was 4±0.5 compared to 2.66±0.3 for control mice, p<0.005).

Example 5

CXCL11 Redirects the Polarization of Antigen Specific Effector-Inflammatory T Cells During the accelerating phase of disease in MOGp33-55/CFA induced EAE, the vast majority of MOGp33-55 CD4+ specific T cells display the IFN-$\gamma^{high}$ IL-$4^{low}$ IL-$10^{low}$ effector phenotype [Goldberg et al., J Immunol (2004) 173:6465-6471]. Therefore, an attempt was made to determine whether CXCL11 redirects the polarization of these antigen specific T cells into IFN-$\gamma^{low}$ IL-$4^{high}$ and/or IFN-$\gamma^{low}$ IL-$10^{high}$ T-reg cells.

Materials and Methods

Animals

Mice were used as described in detail in Example 1 hereinabove.

Induction of Active Disease

Induction of active EAE was effected as described in detail in Example 1 hereinabove.

Generation of CXCL11-hIg Fusion Protein

As described in detail in Example 2, hereinabove.

Generation of Spleen Cells

Primary spleen cells were isolated from EAE induced mice (2 days after the onset of disease). Cells were cultured in a humidified 7.5% $CO_2$ atmosphere at 37° C. and stimulated with their target autoimmune antigen, $MOG_{35-53}$ peptide, at a concentration of 50 μg/ml. Cultures were or were not additionally supplemented with CXCL11-IgG at a concentration of 20 μg/ml.

Flow Cytometry Analysis

Flow cytometry analysis was conducted according to the protocol previously described by Schif-Zuck et al. [Schif-Zuck et al., J Immunol (2005) 174:4307-4315]. Briefly, $10^6$ cells were suspended in 1000 μl dyeing buffer containing an anti CD4-APC (BioLegend, San Diego, Calif.) labeled for 5 minutes on ice. The cells were washed three times in dyeing buffer and resuspended in 100 μl 1% PFA and transferred into FACS tubes.

Intracellular staining of IL-10 was conducted using PE labeled anti-mouse IL-10 (BD Biosciences).

Results

Figures 7A, 7B, 7C, 7D, 7E:
FIGS. 7A-E are bar graphs depicting ex-vivo production of cytokines in primary T cell cultures in response to the target antigen ($MOG_{35-55}$) supplemented or not supplemented with CXCL11-IgG. Cytokine production was determined by ELISA as follows.

FIGS. 7A-E clearly show that in the presence of CXCL11-IgG, antigen specific T cells redirect their polarization into high IL-10, high IL-4, low IFN-γ producing T cells (FIGS. 7A, 7B and 7C, respectively). These cells also produce significantly reduced levels of the pro-inflammatory cytokine TNF-α (FIG. 7D, 178±32 compared to 460±65 pg/ml for untreated T cells, p<0.001). No significant change was observed in TGF-β production (FIG. 7E). Additionally, supplementation of primary T cells with control IgG or β-actin-IgG did not lead to a significant change in cytokine production (data not shown).

Figures 8A, 8B:
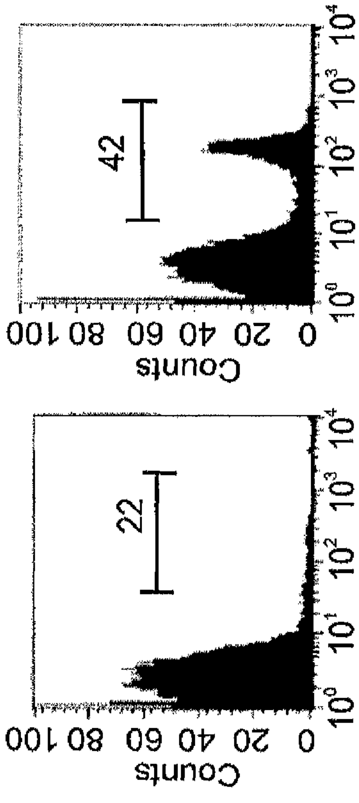
FIGS. 8A-B are histograms of FACS analysis depicting IL-10 producing T cells. Flow cytometry analysis was gated on CD4+ and on IL-10 (horizontal axis).

Flow cytometry analysis (FIGS. 8A and 8B) revealed that only about 2% of CD4+ control T cells (not supplemented with CXCL11-IgG) were polarized into a high IL-10 producing CD4+ T cells. Conversely, MOGp33-55 specific activation in the presence of CXCL11-IgG resulted in a massive skewing into high IL-10 producing CD4+ T cells (42%). Further analysis of these cells revealed that they were $CD4^+$ $CD25^-FOXp3^-$ T cells (data not shown).

Example 6

Primary T Cells Stimulated ex-vivo with CXL11-IgG Suppress Active EAE in Adoptive Transfer Experiments In an attempt to reveal the therapeutic competence on EAE of IFN-$\gamma^{low}$ IL-$4^{high}$ IL-$10^{high}$ T-reg cells (generated following stimulation of primary spleen cells with CXCL11-IgG), adoptive transfer experiments were carried out.

Materials and Methods

Animals

Mice were used as described in detail in Example 1 hereinabove.

Induction of Active Disease

Induction of active EAE was effected as described in detail in Example 1 hereinabove.

Generation of CXCL11-hIg Fusion Protein

As described in detail in Example 2, hereinabove.

Generation of Spleen Cells

Primary spleen cells were isolated from EAE induced mice (2 days after the onset of disease). Cells were cultured in a humidified 7.5% $CO_2$ atmosphere at 37° C. and stimulated with their target autoimmune antigen, $MOG_{35-53}$ peptide, at a concentration of 50 μg/ml. In addition, some of the cultures were supplemented with CXCL11-IgG at a concentration of 20 μg/ml.

Adoptive Transfer of Primary Splenocytes to Recipient EAE Induced Mice

The cultured primary T cells described hereinabove were administered ($30\times10^6$/mouse) to EAE induced recipient mice, just after the onset of disease (on day 11). An additional group of mice received cells previously cultured with CXCL11-IgG followed by repeated (every 3 days) administrations of anti-IL-10 neutralizing antibodies (100 μg/mouse, R&D). This group was monitored for only 10 days to avoid production of xerographic antibodies.

Results

Figure 9:
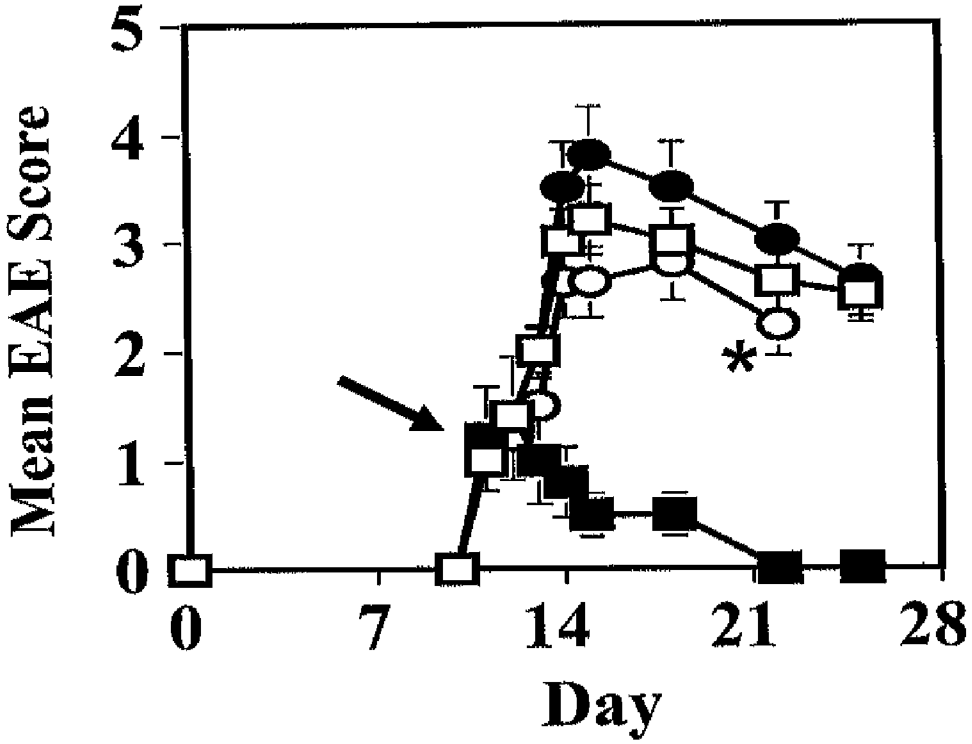
FIG. 9 is a graph depicting the EAE score of mice following transfer of primary T cells from cultures previously cultured with the target antigen ($MOG_{35-55}$) supplemented or not supplemented with CXCL11-IgG. Primary spleen cells were transferred to EAE induced recipient mice, just after the onset of disease (on day 11) as follows: recipients of cells previously cultured with CXCL11IgG (close squares), recipients of cells previously cultured only with $MOG_{35-55}$ (close circles), no treatment (open squares), recipients of cells that following the administration of T cells previously cultured with CXCL11IgG, were administered with anti IL-10 neutralizing antibodies (open circles, * this group was monitored for only 10 days to avoid production of xerographic antibodies). An observer blind to the experimental protocol then monitored the development and progression of disease. The results presented summarize one of two independent experiments with the same pattern of data. Results are shown as mean maximal score of six mice per group±SE.
Figure 10A:
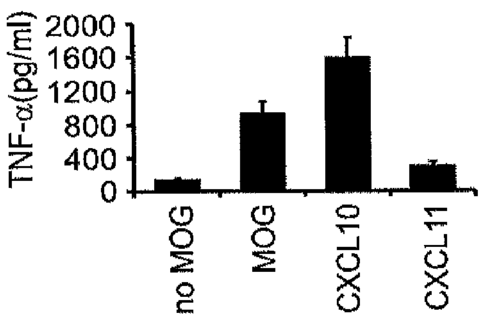
FIGS. 10A-K are bar graphs depicting repolarization of effector and naïve T cells in response to CXCL11 stimulation in vitro.
Figure 10B:
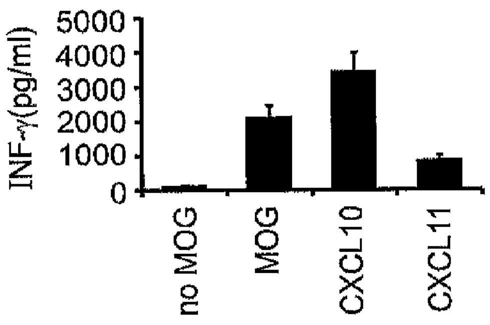
Figure 10C:
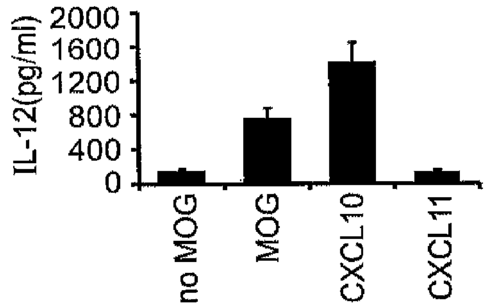
Figure 10D:
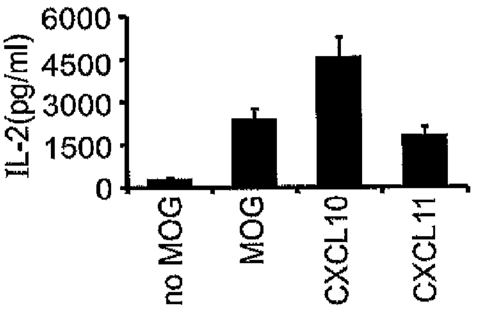
Figure 10E:
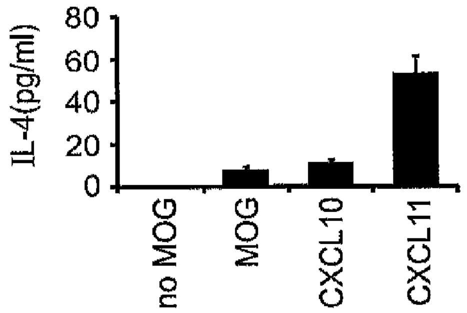
Figure 10F:
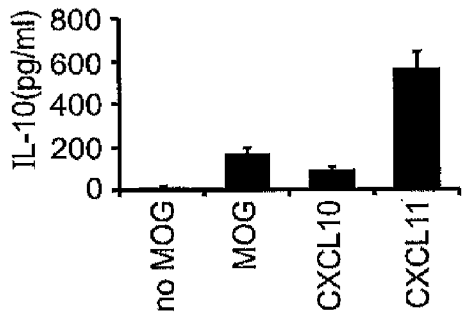
Figure 10G:
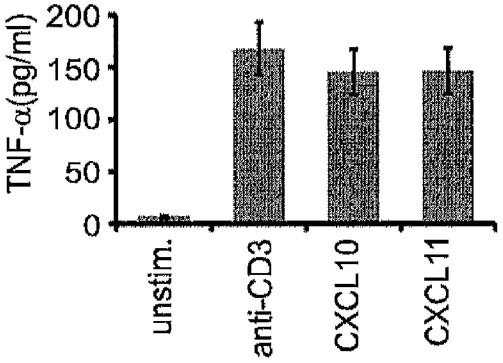
Figure 10H:
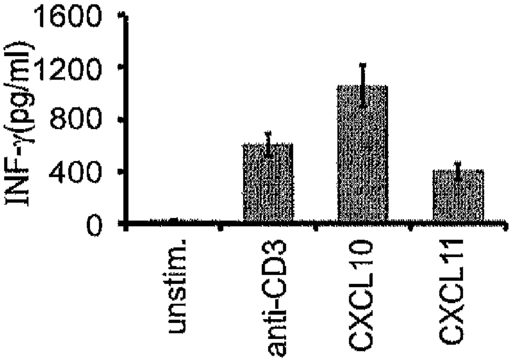
Figure 10I:
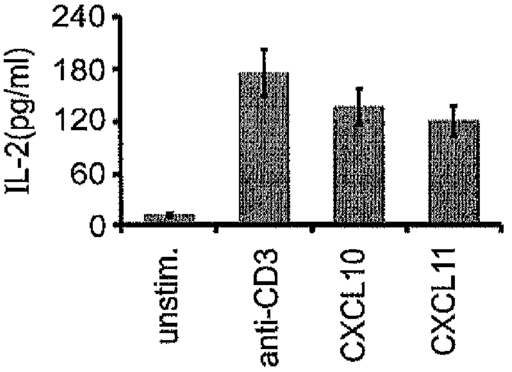
Figure 10J:
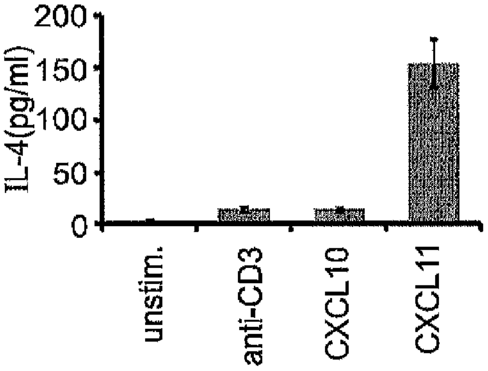
Figure 10K:
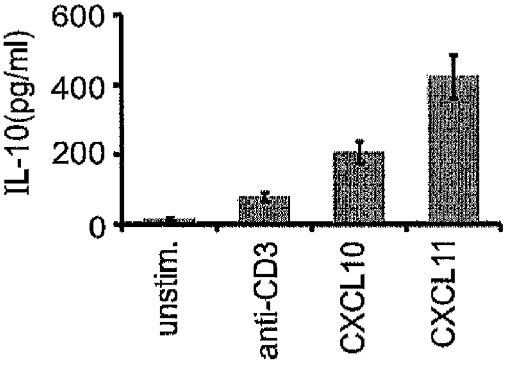

As depicted in FIG. 9, the present inventors showed that administration of control primary T cells (which were cultured in the absence of CXCL11-IgG) aggravated disease severity (on day 15, mean maximal score recorded was 3.8±0.5 compared to 3.2±0.66 for untreated EAE mice, $p<0.05$), while administration of IL-10 producing T cells selected in the presence of CXCL11-IgG lead to a rapid recovery of active EAE (on day 18 mean maximal score recorded was 0.5±0.166 compared to 3.2±0.66 for untreated EAE mice, $p<0.001$). Importantly, repeated administrations of anti-IL-10 antibodies reversed the therapeutic effect of these cells (on day 18 mean maximal score recorded was 2.8±0.6 compared to 3±0.66 for untreated EAE mice). The very same pattern of results were obtained when primary T cells were cultured with commercially available CXCL11 (R&D) showing that these functional activities of CXCL11 are not dependent on its stabilization as a fusion protein (data not shown).

Example 7

CXCL11 Redirects the Polarization of Mouse and Human, Naïve and Effector T Cells into IL-10 Producing T Regulatory Cells Materials and Methods Animals Mice were used as described in detail in Example 1 hereinabove.

Induction of Active Disease

Induction of active EAE was effected as described in detail in Example 1 hereinabove.

Generation of Spleen Cells

Primary spleen cells were isolated from EAE induced C57BL/6 mice (day 9).

Cells ($10^6$ cells/ml) were cultured in a humidified 7.5% $CO_2$ atmosphere at 37° C. for 72 hours and stimulated with their target auto immune antigen, $MOG_{35-53}$ peptide, at a concentration of 50 μg/ml. In addition, the cultures were supplemented with either recombinant mCXCL10 (R&D) or mCXCL11 (R&D) at a concentration of 50 ng/ml.

Isolation of Naïve CD4+ T Cells

Naïve CD4+ T cells were purified from naïve C57BL/6 mice spleens using magnetic beads and were stimulated (300,000 cell/ml) for 48 hours with immobilized anti-CD3ϵ mAb (2 μg/ml, Biolegend) and soluble anti-CD28 mAb (2 μg/ml, Biolegend) in the presence of either rmCXCL10 (R&D) or rmCXCL11 (R&D) at a concentration of 50 ng/ml.

Human T Cells

Human CD4+ T cells were purified from peripheral blood mononuclear cells using anti-CD4 magnetic beads (MACS beads, according the manufacturer protocol) and were stimulated (300,000 cell/ml) for 48 hours with anti-CD3ϵ mAb (2 μg/ml, Biolegend) and soluble anti-CD28 mAb (2 μg/ml, Biolegend) in the presence of 10 ng/ml rhCXCL10 (R&D) or rhCXCL11 (R&D) with or without 0.5 μg/ml of neutralizing anti-CXCR3 antibody (R&D).

ELISA

As described in detail in Example 3, hereinabove.

Results

Figure 11:
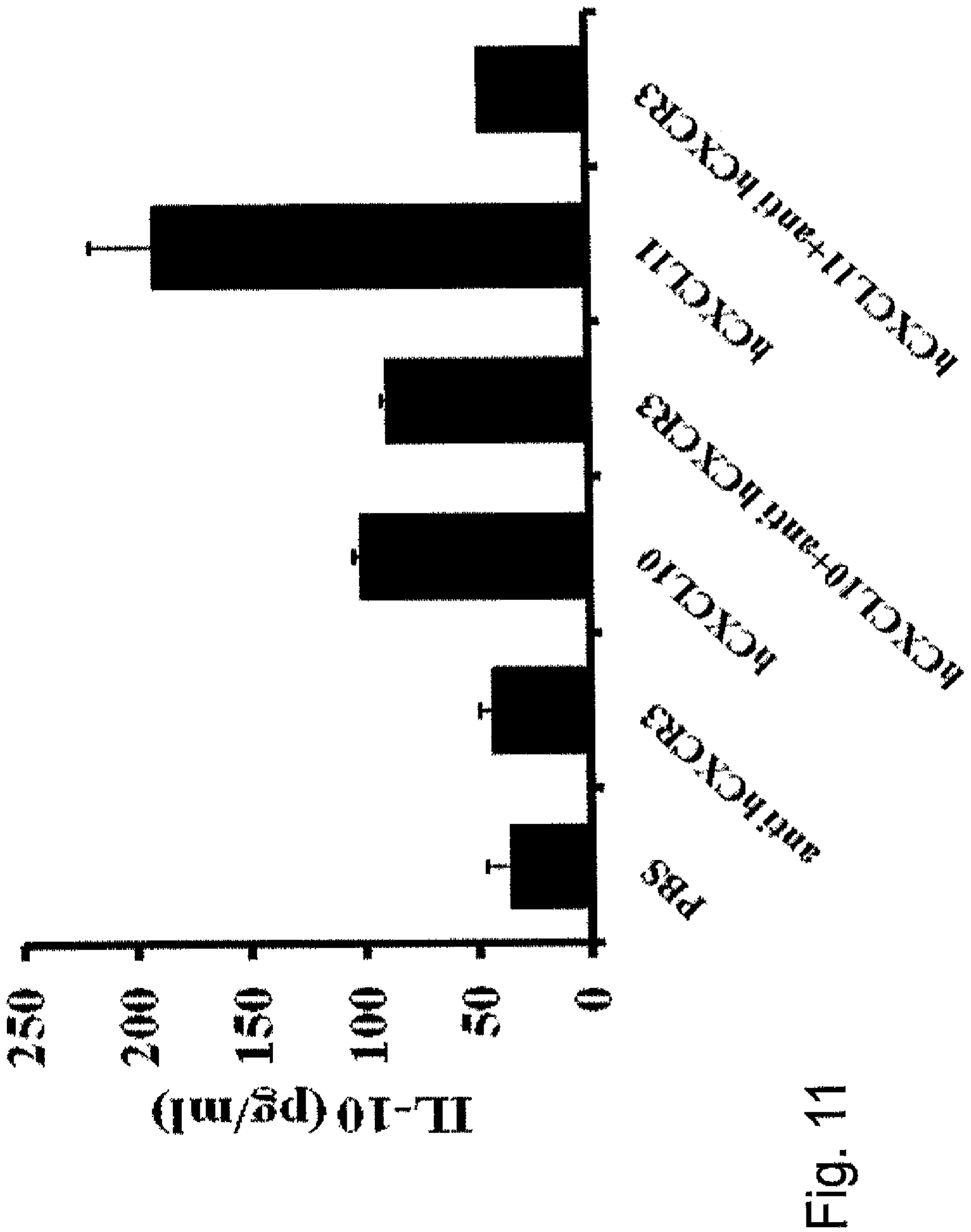
FIG. 11 is a bar graph showing that CXCL11 activity is CXCR3 mediated. Human CD4+ T cells were purified from peripheral blood mononuclear cells using anti-CD4 magnetic beads and were stimulated (300,000 cell/ml) for 48 hours with anti-CD3ε mAb in the presence of either rhCXCL10 or rhCXCL11 (10 ng/ml). Some of the cultures were further supplemented with the neutralizing anti-CXCR3 antibody (0.5 μg/ml). IL-10 levels were determined by ELISA according to manufacturer's protocol. IL-10 levels are shown as mean level±SE.

As shown in FIGS. 10G-K, CXCL11 directly re-polarizes naïve CD4+ T cells undergoing T-cell activation into IL-10 producing regulatory T cells. These results presented a very similar pattern of cytokine secretion as were seen with effector T cells from EAE mice which were activated in vitro by their target antigen in the presence of antigen presenting cells (FIGS. 10A-F and example 5 hereinabove). Similar results were also illustrated with purified human CD4+ cells activated under similar conditions (FIG. 11). It should be noted that mouse and human rCXCL11 were not cross-reactive (results not shown).

Example 8

CXL11 Redirects the Polarization of Human T Cells in a CXCR3 Dependent Manner

In an attempt to elucidate how CXCL11 redirects the polarization of T cells into high IL-10, high IL-4, low IFN-γ producing T cells, experiments utilizing anti-CXCR3 antibodies were carried out.

Materials and Methods

Human T Cells

As described in detail in Example 7, hereinabove.

ELISA

As described in detail in Example 3, hereinabove.

Results

CXCL11 binds two different receptors, CXCR3 and CXCR7, yet it induces migration only via CXCR3 [Burns et al., J Exp Med (2006) 203: 2201-13]. To elucidate the role CXCR3 plays in CXCL11 induced migration and re-polarization of T cells, an anti-CXCR3 blocking was used. First, dose dependent experiments were carried out to determine the in vitro concentration of antibody required for total blockage of CXCL11 induced migration (data not shown). Under these conditions, experiments were carried out to illustrate the contribution of CXCR3 to CXCL11 induced polarization of CD4+ T cells. As clearly shown in FIG. 11, the use of anti-CXCR3 antibody blocked IL-10 production of T cells by approximately 75%, implicating the pivotal role of CXCR3 in CXCL11 re-polarization of T cells.

It is appreciated that certain features of the invention, which are, for clarity, described in the context of separate embodiments, may also be provided in combination in a single embodiment. Conversely, various features of the invention, which axe, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

---

What is claimed is:

1. A method of suppressing disease severity of multiple sclerosis in a subject in need thereof, the method comprising administering to the subject a therapeutically effective amount of CXCL11 (GeneBank Accession No. AAH05292), thereby suppressing disease severity of multiple sclerosis in the subject.

2. The method of claim 1, wherein said CXCL11 (GenBank Accession No. AAH05292) is capable of up-regulating secretion of IL-10 and/or IL-4 from macrophages and T cells.

3. The method of claim 1, wherein said CXCL11 (GenBank Accession No. AAH05292) is capable of down-regulating secretion of a cytokine from macrophages and T cells, wherein said cytokine is selected from the group consisting of TNF-α, IFN-γ, IL-2 and IL-12.

4. The method of claim 1, wherein CXCL11 (GenBank Accession No. AAH05292) is attached to a heterologous amino acid sequence.

5. The method of claim 4, wherein said CXCL11 (GenBank Accession No. AAH05292) attached to said heterologous amino acid sequence is set forth in SEQ ID NO: 6.

* * * * *

SEQUENCE LISTING

```
<160> NUMBER OF SEQ ID NOS: 31

<210> SEQ ID NO 1
<211> LENGTH: 285
<212> TYPE: DNA
<213> ORGANISM: Homo sapiens
<220> FEATURE:
<221> NAME/KEY: misc_feature
<223> OTHER INFORMATION: Human CXCL11

<400> SEQUENCE: 1

atgagtgtga agggcatggc tatagccttg gctgtgatat tgtgtgctac agttgttcaa      60

ggcttcccca tgttcaaaag aggacgctgt ctttgcatag gccctggggt aaaagcagtg     120

aaagtggcag atattgagaa agcctccata atgtacccaa gtaacaactg tgacaaaata     180

gaagtgatta ttaccctgaa agaaaataaa ggacaacgat gcctaaatcc caaatcgaag     240

caagcaaggc ttataatcaa aaaagttgaa agaaagaatt tttaa                    285


<210> SEQ ID NO 2
<211> LENGTH: 94
<212> TYPE: PRT
<213> ORGANISM: Homo sapiens
<220> FEATURE:
<221> NAME/KEY: misc_feature
<223> OTHER INFORMATION: Human CXCL11

<400> SEQUENCE: 2

Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
    50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90
```

<210> SEQ ID NO 3
<211> LENGTH: 714
<212> TYPE: DNA
<213> ORGANISM: Artificial sequence
<220> FEATURE:
<223> OTHER INFORMATION: human Ig derived fragment coding sequence

<400> SEQUENCE: 3
ccgctcgagc ccaaatcttg tgacaaaact cacacatgcc caccgtgccc agcacctgaa 60
ctcctggggg gaccgtcagt cttcctcttc cccccaaaac ccaaggacac cctcatgatc 120
tcccggaccc ctgaggtcac atgcgtggtg gtggacgtga gccacgaaga ccctgaggtc 180
aagttcaact ggtacgtgga cggcgtggag gtgcataatg ccaagacaaa gccgcgggag 240
gagcagtaca acagcacgta ccgtgtggtc agcgtcctca ccgtcctgca ccaggactgg 300
ctgaatggca aggagtacaa gtgcaaggtc tccaacaaag ccctcccagc ccccatcgag 360
aaaaccatct ccaaagccaa agggcagccc cgagaaccac aggtgtacac cctgccccca 420
tcccgggagg agatgaccaa gaaccaggtc agcctgacct gcctggtcaa aggcttctat 480
cccagcgaca tcgccgtgga gtgggagagc aatgggcagc cggagaacaa ctacaagacc 540
acgcctcccg tgctggactc cgacggctcc ttcttcctct atagcaagct caccgtggac 600
aagagcaggt ggcagcaggg gaacgtcttc tcatgctccg tgatgcatga ggctctgcac 660
aaccactaca cgcagaagag cctctccctg tccccgggta aagggcccga acaa 714

<210> SEQ ID NO 4
<211> LENGTH: 238
<212> TYPE: PRT
<213> ORGANISM: Artificial sequence
<220> FEATURE:
<223> OTHER INFORMATION: human Ig derived fragment

<400> SEQUENCE: 4

Pro Leu Glu Pro Lys Ser Cys Asp Lys Thr His Thr Cys Pro Pro Cys
1 5 10 15

Pro Ala Pro Glu Leu Leu Gly Gly Pro Ser Val Phe Leu Phe Pro Pro
20 25 30

Lys Pro Lys Asp Thr Leu Met Ile Ser Arg Thr Pro Glu Val Thr Cys
35 40 45

Val Val Val Asp Val Ser His Glu Asp Pro Glu Val Lys Phe Asn Trp
50 55 60

Tyr Val Asp Gly Val Glu Val His Asn Ala Lys Thr Lys Pro Arg Glu
65 70 75 80

Glu Gln Tyr Asn Ser Thr Tyr Arg Val Val Ser Val Leu Thr Val Leu
85 90 95

His Gln Asp Trp Leu Asn Gly Lys Glu Tyr Lys Cys Lys Val Ser Asn
100 105 110

Lys Ala Leu Pro Ala Pro Ile Glu Lys Thr Ile Ser Lys Ala Lys Gly
115 120 125

Gln Pro Arg Glu Pro Gln Val Tyr Thr Leu Pro Pro Ser Arg Glu Glu
130 135 140

Met Thr Lys Asn Gln Val Ser Leu Thr Cys Leu Val Lys Gly Phe Tyr
145 150 155 160

Pro Ser Asp Ile Ala Val Glu Trp Glu Ser Asn Gly Gln Pro Glu Asn
165 170 175

Asn Tyr Lys Thr Thr Pro Pro Val Leu Asp Ser Asp Gly Ser Phe Phe
180 185 190

```
Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
    210                 215                 220

Gln Lys Ser Leu Ser Leu Ser Pro Gly Lys Gly Pro Glu Gln
225                 230                 235


<210> SEQ ID NO 5
<211> LENGTH: 996
<212> TYPE: DNA
<213> ORGANISM: Artificial sequence
<220> FEATURE:
<223> OTHER INFORMATION: Human CXCL11-Ig fusion protein coding sequence

<400> SEQUENCE: 5

atgagtgtga agggcatggc tatagccttg gctgtgatat tgtgtgctac agttgttcaa     60

ggcttcccca tgttcaaaag aggacgctgt ctttgcatag gccctggggt aaaagcagtg    120

aaagtggcag atattgagaa agcctccata atgtacccaa gtaacaactg tgacaaaata    180

gaagtgatta ttaccctgaa agaaaataaa ggacaacgat gcctaaatcc caaatcgaag    240

caagcaaggc ttataatcaa aaaagttgaa agaaagaatt ttccgctcga gcccaaatct    300

tgtgacaaaa ctcacacatg cccaccgtgc ccagcacctg aactcctggg gggaccgtca    360

gtcttcctct tccccccaaa acccaaggac accctcatga tctcccggac ccctgaggtc    420

acatgcgtgg tggtggacgt gagccacgaa gaccctgagg tcaagttcaa ctggtacgtg    480

gacggcgtgg aggtgcataa tgccaagaca aagccgcggg aggagcagta caacagcacg    540

taccgtgtgg tcagcgtcct caccgtcctg caccaggact ggctgaatgg caaggagtac    600

aagtgcaagg tctccaacaa agccctccca gcccccatcg agaaaaccat ctccaaagcc    660

aaagggcagc cccgagaacc acaggtgtac accctgcccc catcccggga ggagatgacc    720

aagaaccagg tcagcctgac ctgcctggtc aaaggcttct atcccagcga catcgccgtg    780

gagtgggaga gcaatgggca gccggagaac aactacaaga ccacgcctcc cgtgctggac    840

tccgacggct ccttcttcct ctatagcaag ctcaccgtgg acaagagcag gtggcagcag    900

gggaacgtct tctcatgctc cgtgatgcat gaggctctgc acaaccacta cacgcagaag    960

agcctctccc tgtccccggg taaagggccc gaacaa                              996


<210> SEQ ID NO 6
<211> LENGTH: 332
<212> TYPE: PRT
<213> ORGANISM: Artificial sequence
<220> FEATURE:
<223> OTHER INFORMATION: Human CXCL11-Ig fusion protein

<400> SEQUENCE: 6

Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
    50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe Pro Leu
                85                  90                  95
```

```
Glu Pro Lys Ser Cys Asp Lys Thr His Thr Cys Pro Pro Cys Pro Ala
            100                 105                 110

Pro Glu Leu Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220

Arg Glu Pro Gln Val Tyr Thr Leu Pro Pro Ser Arg Glu Glu Met Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
        275                 280                 285

Ser Lys Leu Thr Val Asp Lys Ser Arg Trp Gln Gln Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Pro Gly Lys Gly Pro Glu Gln
                325                 330


<210> SEQ ID NO 7
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 7

ctcgagccca aatcttgtga caaaac                                            26


<210> SEQ ID NO 8
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 8

gggcccttta cccggggaca gggaga                                            26


<210> SEQ ID NO 9
<211> LENGTH: 303
<212> TYPE: DNA
<213> ORGANISM: Mus musculus
<220> FEATURE:
<221> NAME/KEY: misc_feature
<223> OTHER INFORMATION: Murine CXCL11
```

<400> SEQUENCE: 9
atgaacagga aggtcacagc catagccctg gctgcgatca tctgggccac agctgctcaa 60
ggcttcctta tgttcaaaca ggggcgctgt ctttgcatcg gccccgggat gaaagccgtc 120
aaaatggcag agatcgagaa agcttctgta atttacccga gtaacggctg cgacaaagtt 180
gaagtgattg ttactatgaa ggctcataaa cgacaaaggt gcctggaccc cagatccaag 240
caagctcgcc tcataatgca ggcaatagaa aaaaagaatt ttttaaggcg tcaaaacatg 300
tga 303

<210> SEQ ID NO 10
<211> LENGTH: 94
<212> TYPE: PRT
<213> ORGANISM: Mus musculus
<220> FEATURE:
<221> NAME/KEY: misc_feature
<223> OTHER INFORMATION: Murine CXCL11

<400> SEQUENCE: 10

```
Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
    50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90
```

<210> SEQ ID NO 11
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 11
gctagcatga acaggaaggt cacagccata gc 32

<210> SEQ ID NO 12
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 12
ctcgagcatg ttttgacgcc ttaaaaaatt 30

<210> SEQ ID NO 13
<211> LENGTH: 1002
<212> TYPE: DNA
<213> ORGANISM: Artificial sequence
<220> FEATURE:
<223> OTHER INFORMATION: Murine CXCL11-Ig fusion coding sequence

<400> SEQUENCE: 13
atgaacagga aggtcacagc catagccctg gctgcgatca tctgggccac agctgctcaa 60
ggcttcctta tgttcaaaca ggggcgctgt ctttgcatcg gccccgggat gaaagccgtc 120

-continued

```
aaaatggcag agatcgagaa agcttctgta atttacccga gtaacggctg cgacaaagtt    180

gaagtgattg ttactatgaa ggctcataaa cgacaaaggt gcctggaccc cagatccaag    240

caagctcgcc tcataatgca ggcaatagaa aaaaagaatt ttttaaggcg tcaaaacatg    300

ccgctcgagg tgcccaggga ttgtggttgt aagccttgca tatgtacagt cccagaagta    360

tcatctgtct tcatcttccc cccaaagccc aaggatgtgc tcaccattac tctgactcct    420

aaggtcacgt gtgttgtggt agacatcagc aaggatgatc ccgaggtcca gttcagctgg    480

tttgtagatg atgtggaggt gcacacagct cagacgcaac cccgggagga gcagttcaac    540

agcactttcc gctcagtcag tgaacttccc atcatgcacc aggactgcct caatggcaag    600

gagttcaaat gcagggtcaa cagtgcagct ttccctgccc ccatcgagaa aaccatctcc    660

aaaaccaaag gcagaccgaa ggctccacag gtgtacacca ttccacctcc caaggagcag    720

atggccaagg ataaagtcag tctgacctgc atgataacag acttcttccc tgaagacatt    780

actgtggagt ggcagtggaa tgggcagcca gcggagaact acaagaacac tcagcccatc    840

atggacacag atggctctta cttcgtctac agcaagctca atgtgcagaa gagcaactgg    900

gaggcaggaa atactttcac ctgctctgtg ttacatgagg gcctgcacaa ccaccatact    960

gagaagagcc tctcccactc tcctggtaaa gggcccgaac aa                      1002
```

<210> SEQ ID NO 14
<211> LENGTH: 334
<212> TYPE: PRT
<213> ORGANISM: Artificial sequence
<220> FEATURE:
<223> OTHER INFORMATION: Murine CXCL11-Ig fusion protein

<400> SEQUENCE: 14

```
Met Asn Arg Lys Val Thr Ala Ile Ala Leu Ala Ala Ile Ile Trp Ala
1               5                   10                  15

Thr Ala Ala Gln Gly Phe Leu Met Phe Lys Gln Gly Arg Cys Leu Cys
            20                  25                  30

Ile Gly Pro Gly Met Lys Ala Val Lys Met Ala Glu Ile Glu Lys Ala
        35                  40                  45

Ser Val Ile Tyr Pro Ser Asn Gly Cys Asp Lys Val Glu Val Ile Val
    50                  55                  60

Thr Met Lys Ala His Lys Arg Gln Arg Cys Leu Asp Pro Arg Ser Lys
65                  70                  75                  80

Gln Ala Arg Leu Ile Met Gln Ala Ile Glu Lys Lys Asn Phe Leu Arg
                85                  90                  95

Arg Gln Asn Met Pro Leu Glu Val Pro Arg Asp Cys Gly Cys Lys Pro
            100                 105                 110

Cys Ile Cys Thr Val Pro Glu Val Ser Ser Val Phe Ile Phe Pro Pro
        115                 120                 125

Lys Pro Lys Asp Val Leu Thr Ile Thr Leu Thr Pro Lys Val Thr Cys
    130                 135                 140

Val Val Val Asp Ile Ser Lys Asp Asp Pro Glu Val Gln Phe Ser Trp
145                 150                 155                 160

Phe Val Asp Asp Val Glu Val His Thr Ala Gln Thr Gln Pro Arg Glu
                165                 170                 175

Glu Gln Phe Asn Ser Thr Phe Arg Ser Val Ser Glu Leu Pro Ile Met
            180                 185                 190

His Gln Asp Cys Leu Asn Gly Lys Glu Phe Lys Cys Arg Val Asn Ser
        195                 200                 205
```

Ala Ala Phe Pro Ala Pro Ile Glu Lys Thr Ile Ser Lys Thr Lys Gly
    210                 215                 220

Arg Pro Lys Ala Pro Gln Val Tyr Thr Ile Pro Pro Pro Lys Glu Gln
225                 230                 235                 240

Met Ala Lys Asp Lys Val Ser Leu Thr Cys Met Ile Thr Asp Phe Phe
                245                 250                 255

Pro Glu Asp Ile Thr Val Glu Trp Gln Trp Asn Gly Gln Pro Ala Glu
            260                 265                 270

Asn Tyr Lys Asn Thr Gln Pro Ile Met Asp Thr Asp Gly Ser Tyr Phe
        275                 280                 285

Val Tyr Ser Lys Leu Asn Val Gln Lys Ser Asn Trp Glu Ala Gly Asn
    290                 295                 300

Thr Phe Thr Cys Ser Val Leu His Glu Gly Leu His Asn His His Thr
305                 310                 315                 320

Glu Lys Ser Leu Ser His Ser Pro Gly Lys Gly Pro Glu Gln
                325                 330

<210> SEQ ID NO 15
<211> LENGTH: 297
<212> TYPE: DNA
<213> ORGANISM: Mus musculus
<220> FEATURE:
<221> NAME/KEY: misc_feature
<223> OTHER INFORMATION: CXCL10

<400> SEQUENCE: 15
atgaacccaa gtgctgccgt cattttctgc ctcatcctgc tgggtctgag tgggactcaa 60
gggatccctc tcgcaaggac ggtccgctgc aactgcatcc atatcgatga cgggccagtg 120
agaatgaggg ccatagggaa gcttgaaatc atccctgcga gcctatcctg cccacgtgtt 180
gagatcattg ccacgatgaa aaagaatgat gagcagagat gtctgaatcc ggaatctaag 240
accatcaaga atttaatgaa agcgtttagc caaaaaaggt ctaaaagggc tccttaa 297

<210> SEQ ID NO 16
<211> LENGTH: 98
<212> TYPE: PRT
<213> ORGANISM: Mus musculus
<220> FEATURE:
<221> NAME/KEY: misc_feature
<223> OTHER INFORMATION: CXCL10

<400> SEQUENCE: 16

Met Asn Pro Ser Ala Ala Val Ile Phe Cys Leu Ile Leu Leu Gly Leu
1               5                   10                  15

Ser Gly Thr Gln Gly Ile Pro Leu Ala Arg Thr Val Arg Cys Asn Cys
            20                  25                  30

Ile His Ile Asp Asp Gly Pro Val Arg Met Arg Ala Ile Gly Lys Leu
        35                  40                  45

Glu Ile Ile Pro Ala Ser Leu Ser Cys Pro Arg Val Glu Ile Ile Ala
    50                  55                  60

Thr Met Lys Lys Asn Asp Glu Gln Arg Cys Leu Asn Pro Glu Ser Lys
65                  70                  75                  80

Thr Ile Lys Asn Leu Met Lys Ala Phe Ser Gln Lys Arg Ser Lys Arg
                85                  90                  95

Ala Pro

<210> SEQ ID NO 17
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 17
gctagcatga acccaagtgc tgccgtcatt tt 32

<210> SEQ ID NO 18
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 18
ctcgagagga gcccttttag accttttttg 30

<210> SEQ ID NO 19
<211> LENGTH: 1008
<212> TYPE: DNA
<213> ORGANISM: Artificial sequence
<220> FEATURE:
<223> OTHER INFORMATION: Murine CXCL10-Ig fusion coding sequence

<400> SEQUENCE: 19
atgaacccaa gtgctgccgt cattttctgc ctcatcctgc tgggtctgag tgggactcaa 60
gggatccctc tcgcaaggac ggtccgctgc aactgcatcc atatcgatga cgggccagtg 120
agaatgaggg ccatagggaa gcttgaaatc atccctgcga gcctatcctg cccacgtgtt 180
gagatcattg ccacgatgaa aaagaatgat gagcagagat gtctgaatcc ggaatctaag 240
accatcaaga atttaatgaa agcgtttagc caaaaaaggt ctaaaagggc tcctccgctc 300
gagcccaaat cttgtgacaa aactcacaca tgcccaccgt gcccagcacc tgaactcctg 360
gggggaccgt cagtcttcct cttcccccca aaacccaagg acaccctcat gatctcccgg 420
acccctgagg tcacatgcgt ggtggtggac gtgagccacg aagaccctga ggtcaagttc 480
aactggtacg tggacggcgt ggaggtgcat aatgccaaga caaagccgcg ggaggagcag 540
tacaacagca cgtaccgtgt ggtcagcgtc ctcaccgtcc tgcaccagga ctggctgaat 600
ggcaaggagt acaagtgcaa ggtctccaac aaagccctcc cagcccccat cgagaaaacc 660
atctccaaag ccaaagggca gccccgagaa ccacaggtgt acaccctgcc cccatcccgg 720
gaggagatga ccaagaacca ggtcagcctg acctgcctgg tcaaaggctt ctatcccagc 780
gacatcgccg tggagtggga gagcaatggg cagccggaga acaactacaa gaccacgcct 840
cccgtgctgg actccgacgg ctccttcttc ctctatagca agctcaccgt ggacaagagc 900
aggtggcagc aggggaacgt cttctcatgc tccgtgatgc atgaggctct gcacaaccac 960
tacacgcaga agagcctctc cctgtccccg ggtaaagggc ccgaacaa 1008

<210> SEQ ID NO 20
<211> LENGTH: 336
<212> TYPE: PRT
<213> ORGANISM: Artificial sequence
<220> FEATURE:
<223> OTHER INFORMATION: Murine CXCL10-Ig fusion protein

<400> SEQUENCE: 20

Met Asn Pro Ser Ala Ala Val Ile Phe Cys Leu Ile Leu Leu Gly Leu
1 5 10 15

Ser Gly Thr Gln Gly Ile Pro Leu Ala Arg Thr Val Arg Cys Asn Cys
20 25 30

Ile His Ile Asp Asp Gly Pro Val Arg Met Arg Ala Ile Gly Lys Leu
35 40 45

Glu Ile Ile Pro Ala Ser Leu Ser Cys Pro Arg Val Glu Ile Ile Ala
50 55 60

Thr Met Lys Lys Asn Asp Glu Gln Arg Cys Leu Asn Pro Glu Ser Lys
65 70 75 80

Thr Ile Lys Asn Leu Met Lys Ala Phe Ser Gln Lys Arg Ser Lys Arg
85 90 95

Ala Pro Pro Leu Glu Pro Lys Ser Cys Asp Lys Thr His Thr Cys Pro
100 105 110

Pro Cys Pro Ala Pro Glu Leu Leu Gly Gly Pro Ser Val Phe Leu Phe
115 120 125

Pro Pro Lys Pro Lys Asp Thr Leu Met Ile Ser Arg Thr Pro Glu Val
130 135 140

Thr Cys Val Val Val Asp Val Ser His Glu Asp Pro Glu Val Lys Phe
145 150 155 160

Asn Trp Tyr Val Asp Gly Val Glu Val His Asn Ala Lys Thr Lys Pro
165 170 175

Arg Glu Glu Gln Tyr Asn Ser Thr Tyr Arg Val Val Ser Val Leu Thr
180 185 190

Val Leu His Gln Asp Trp Leu Asn Gly Lys Glu Tyr Lys Cys Lys Val
195 200 205

Ser Asn Lys Ala Leu Pro Ala Pro Ile Glu Lys Thr Ile Ser Lys Ala
210 215 220

Lys Gly Gln Pro Arg Glu Pro Gln Val Tyr Thr Leu Pro Pro Ser Arg
225 230 235 240

Glu Glu Met Thr Lys Asn Gln Val Ser Leu Thr Cys Leu Val Lys Gly
245 250 255

Phe Tyr Pro Ser Asp Ile Ala Val Glu Trp Glu Ser Asn Gly Gln Pro
260 265 270

Glu Asn Asn Tyr Lys Thr Thr Pro Pro Val Leu Asp Ser Asp Gly Ser
275 280 285

Phe Phe Leu Tyr Ser Lys Leu Thr Val Asp Lys Ser Arg Trp Gln Gln
290 295 300

Gly Asn Val Phe Ser Cys Ser Val Met His Glu Ala Leu His Asn His
305 310 315 320

Tyr Thr Gln Lys Ser Leu Ser Leu Ser Pro Gly Lys Gly Pro Glu Gln
325 330 335

<210> SEQ ID NO 21
<211> LENGTH: 702
<212> TYPE: DNA
<213> ORGANISM: Artificial sequence
<220> FEATURE:
<223> OTHER INFORMATION: Murine Ig derived fragment coding sequence

<400> SEQUENCE: 21
ccgctcgagg tgcccaggga ttgtggttgt aagccttgca tatgtacagt cccagaagta 60
tcatctgtct tcatcttccc cccaaagccc aaggatgtgc tcaccattac tctgactcct 120
aaggtcacgt gtgttgtggt agacatcagc aaggatgatc ccgaggtcca gttcagctgg 180

-continued

```
tttgtagatg atgtggaggt gcacacagct cagacgcaac cccgggagga gcagttcaac    240

agcactttcc gctcagtcag tgaacttccc atcatgcacc aggactgcct caatggcaag    300

gagttcaaat gcagggtcaa cagtgcagct ttccctgccc ccatcgagaa aaccatctcc    360

aaaaccaaag gcagaccgaa ggctccacag gtgtacacca ttccacctcc caaggagcag    420

atggccaagg ataaagtcag tctgacctgc atgataacag acttcttccc tgaagacatt    480

actgtggagt ggcagtggaa tgggcagcca gcggagaact acaagaacac tcagcccatc    540

atggacacag atggctctta cttcgtctac agcaagctca atgtgcagaa gagcaactgg    600

gaggcaggaa atactttcac ctgctctgtg ttacatgagg gcctgcacaa ccaccatact    660

gagaagagcc tctcccactc tcctggtaaa gggcccgaac aa                        702


<210> SEQ ID NO 22
<211> LENGTH: 234
<212> TYPE: PRT
<213> ORGANISM: Artificial sequence
<220> FEATURE:
<223> OTHER INFORMATION: Murine Ig derived fragment

<400> SEQUENCE: 22

Pro Leu Glu Val Pro Arg Asp Cys Gly Cys Lys Pro Cys Ile Cys Thr
1               5                   10                  15

Val Pro Glu Val Ser Ser Val Phe Ile Phe Pro Pro Lys Pro Lys Asp
            20                  25                  30

Val Leu Thr Ile Thr Leu Thr Pro Lys Val Thr Cys Val Val Val Asp
        35                  40                  45

Ile Ser Lys Asp Asp Pro Glu Val Gln Phe Ser Trp Phe Val Asp Asp
    50                  55                  60

Val Glu Val His Thr Ala Gln Thr Gln Pro Arg Glu Glu Gln Phe Asn
65                  70                  75                  80

Ser Thr Phe Arg Ser Val Ser Glu Leu Pro Ile Met His Gln Asp Cys
                85                  90                  95

Leu Asn Gly Lys Glu Phe Lys Cys Arg Val Asn Ser Ala Ala Phe Pro
            100                 105                 110

Ala Pro Ile Glu Lys Thr Ile Ser Lys Thr Lys Gly Arg Pro Lys Ala
        115                 120                 125

Pro Gln Val Tyr Thr Ile Pro Pro Pro Lys Glu Gln Met Ala Lys Asp
    130                 135                 140

Lys Val Ser Leu Thr Cys Met Ile Thr Asp Phe Phe Pro Glu Asp Ile
145                 150                 155                 160

Thr Val Glu Trp Gln Trp Asn Gly Gln Pro Ala Glu Asn Tyr Lys Asn
                165                 170                 175

Thr Gln Pro Ile Met Asp Thr Asp Gly Ser Tyr Phe Val Tyr Ser Lys
            180                 185                 190

Leu Asn Val Gln Lys Ser Asn Trp Glu Ala Gly Asn Thr Phe Thr Cys
        195                 200                 205

Ser Val Leu His Glu Gly Leu His Asn His His Thr Glu Lys Ser Leu
    210                 215                 220

Ser His Ser Pro Gly Lys Gly Pro Glu Gln
225                 230


<210> SEQ ID NO 23
<211> LENGTH: 29
<212> TYPE: DNA
<213> ORGANISM: Artificial sequence
<220> FEATURE:
<223> OTHER INFORMATION: Single strand DNA oligonucleotide
```

<400> SEQUENCE: 23
ccgctcgagg tgcccaggga ttgtggttg 29

<210> SEQ ID NO 24
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 24
ttgttcgggc cctttaccag gagagtggga ga 32

<210> SEQ ID NO 25
<211> LENGTH: 2739
<212> TYPE: DNA
<213> ORGANISM: Mus musculus

<400> SEQUENCE: 25
atggtggact accacgcagc gaaccaggcg taccagtacg gcccgaacag cggcggcggc 60
aatggcgcgg gtggcggcgg aagcatgggc gactacatgg cccaggagga tgactgggac 120
cgggacctgc tgttggaccc ggcctgggag aagcagcagc gcaagacctt cacagcctgg 180
tgcaactctc atcttcggaa ggctggcact cagatcgaga atatcgatga ggacttcagg 240
gatgggctca aacttatgct tctgttggag gtcatttcag gggagcgttt gcctaagcca 300
gagcggggga agatgcgagt gcacaagatc aacaatgtaa acaaagccct ggacttcatc 360
gccagcaagg gagtcaagct ggtgtccatc ggggcagaag agattgtgga tggcaatgca 420
aagatgaccc tgggaatgat ctggaccatc atcctcagat ttgccatcca ggacatctct 480
gtggaagaga cctctgctaa ggaaggactc ctcctctggt gccagagaaa gacagcccca 540
tataaaaacg tcaacgtcca gaacttccat atcagctgga aggacgggct ggccttcaat 600
gcactcatcc accggcacag gcctgagctg attgagtatg acaagctgcg gaaggatgat 660
ccagtcacca acctaaacaa tgcatttgaa gtggctgaga aatacctcga tatccccaag 720
atgttggatg ctgaggacat cgtgaacaca gcccggcccg acgagaaggc cataatgaca 780
tatgtgtcca gcttctacca tgccttttca ggagcgcaga aggctgagac cgctgccaac 840
cggatctgca aggtgctggc tgtgaaccag gaaaatgagc acctgatgga agactatgaa 900
cgcctggcca gtgatcttct agagtggatt cggcgcacca tcccctggct ggaggaccgg 960
gtgcctcaga agaccatcca ggaaatgcag cagaagctgg aggacttccg agactatagg 1020
cgtgtgcaca agccgcccaa ggtgcaggag aagtgtcagc tggagatcaa cttcaacaca 1080
ctgcagacca agctgcggct cagcaaccgg cctgccttca tgccctccga gggcaggatg 1140
gtctccgaca tcaacaatgg atggcagcac ctggagcagg ctgagaaggg ctatgaagaa 1200
tggctgctga atgaaatccg taggctggaa cggcttgacc acctggcaga gaagttccgg 1260
cagaaggctt ccatccacga ggcctggact gatgggaagg aggccatgct gaagcaacgg 1320
gactacgaga cagccaccct gtcagacatc aaagctctga tccgaaaaca tgaggccttt 1380
gaaagtgacc tggctgcaca ccaggaccga gtggagcaga ttgctgcaat tgctcaggag 1440
ctcaacgagc tggactacta tgactcccac aacgtcaaca cacggtgcca gaagatctgc 1500
gaccagtggg ataacctggg ctctctgaca cacagtcgca gggaagcctt ggagaaaaca 1560
gagaaacagc tagagaccat cgaccagcta catttggagt atgccaagcg ggctgcaccc 1620
ttcaacaact ggatggagag tgccatggag gacctgcagg acatgttcat cgtccacacc 1680

-continued atcgaggaga tcgagggcct gatctcagcc catgaccagt tcaagtccac cctgccagat 1740
gctgacaggg agcgtgaggc catcctggcc atccacaagg aggcccagag gatcgctgag 1800
agcaatcaca tcaagctgtc gggcagcaat ccctacacca ctgttacccc ccagatcatc 1860
aactccaagt gggagaaggt gcagcagctg gtgccaaaga gggaccatgc actcctggag 1920
gagcagagca agcagcaatc caatgagcac cttcgccgac agttcgccag ccaagccaat 1980
atggtggggc cgtggatcca gaccaagatg gaggagatcg ggcgcatctc cattgagatg 2040
aacgggactc tggaagacca gctgagccac ctgaagcagt acgagcgcag catcgtggac 2100
tacaagccca gcctggacct gctggagcag cagcaccagc tcatccagga ggccctcatc 2160
ttcgacaaca agcacaccaa ctacacaatg gagcatatcc gtgtgggctg ggagcagctg 2220
ctcacgacca ttgcccgcac catcaatgag gtggaaaacc agatcctcac ccgagatgcc 2280
aagggtatca gccaggagca gatgcaggag ttccgggcat ccttcaacca ttttgacaag 2340
gaccatggcg gggcactggg gcctgaggaa ttcaaggcct gcctcatcag cctgggctat 2400
gacgtggaga atgaccggca gggtgatgct gagttcaacc ggatcatgag tgtggttgat 2460
cccaaccata gtggcctcgt gaccttccaa gccttcattg acttcatgtc aagggagacc 2520
acagacacag acacagctga tcaggtcatc gcctccttca aggtcctggc aggagacaag 2580
aacttcatca ctgctgagga actgcggaga gagctgcccc ccgaccaggc cgagtactgc 2640
atcgcccgca tggcacccta ccaggggcct gatgctgctc ctggcgccct tgactacaag 2700
tccttctcca cagccctcta tggggagagc gacctgtga 2739

<210> SEQ ID NO 26
<211> LENGTH: 912
<212> TYPE: PRT
<213> ORGANISM: Mus musculus

<400> SEQUENCE: 26

Met Val Asp Tyr His Ala Ala Asn Gln Ala Tyr Gln Tyr Gly Pro Asn
1               5                   10                  15

Ser Gly Gly Gly Asn Gly Ala Gly Gly Gly Gly Ser Met Gly Asp Tyr
            20                  25                  30

Met Ala Gln Glu Asp Asp Trp Asp Arg Asp Leu Leu Leu Asp Pro Ala
        35                  40                  45

Trp Glu Lys Gln Gln Arg Lys Thr Phe Thr Ala Trp Cys Asn Ser His
    50                  55                  60

Leu Arg Lys Ala Gly Thr Gln Ile Glu Asn Ile Asp Glu Asp Phe Arg
65                  70                  75                  80

Asp Gly Leu Lys Leu Met Leu Leu Leu Glu Val Ile Ser Gly Glu Arg
                85                  90                  95

Leu Pro Lys Pro Glu Arg Gly Lys Met Arg Val His Lys Ile Asn Asn
            100                 105                 110

Val Asn Lys Ala Leu Asp Phe Ile Ala Ser Lys Gly Val Lys Leu Val
        115                 120                 125

Ser Ile Gly Ala Glu Glu Ile Val Asp Gly Asn Ala Lys Met Thr Leu
    130                 135                 140

Gly Met Ile Trp Thr Ile Ile Leu Arg Phe Ala Ile Gln Asp Ile Ser
145                 150                 155                 160

Val Glu Glu Thr Ser Ala Lys Glu Gly Leu Leu Leu Trp Cys Gln Arg
                165                 170                 175

Lys Thr Ala Pro Tyr Lys Asn Val Asn Val Gln Asn Phe His Ile Ser
            180                 185                 190

-continued

```
Trp Lys Asp Gly Leu Ala Phe Asn Ala Leu Ile His Arg His Arg Pro
        195                 200                 205

Glu Leu Ile Glu Tyr Asp Lys Leu Arg Lys Asp Asp Pro Val Thr Asn
    210                 215                 220

Leu Asn Asn Ala Phe Glu Val Ala Glu Lys Tyr Leu Asp Ile Pro Lys
225                 230                 235                 240

Met Leu Asp Ala Glu Asp Ile Val Asn Thr Ala Arg Pro Asp Glu Lys
                245                 250                 255

Ala Ile Met Thr Tyr Val Ser Ser Phe Tyr His Ala Phe Ser Gly Ala
            260                 265                 270

Gln Lys Ala Glu Thr Ala Ala Asn Arg Ile Cys Lys Val Leu Ala Val
        275                 280                 285

Asn Gln Glu Asn Glu His Leu Met Glu Asp Tyr Glu Arg Leu Ala Ser
    290                 295                 300

Asp Leu Leu Glu Trp Ile Arg Arg Thr Ile Pro Trp Leu Glu Asp Arg
305                 310                 315                 320

Val Pro Gln Lys Thr Ile Gln Glu Met Gln Gln Lys Leu Glu Asp Phe
                325                 330                 335

Arg Asp Tyr Arg Arg Val His Lys Pro Pro Lys Val Gln Glu Lys Cys
            340                 345                 350

Gln Leu Glu Ile Asn Phe Asn Thr Leu Gln Thr Lys Leu Arg Leu Ser
        355                 360                 365

Asn Arg Pro Ala Phe Met Pro Ser Glu Gly Arg Met Val Ser Asp Ile
    370                 375                 380

Asn Asn Gly Trp Gln His Leu Glu Gln Ala Glu Lys Gly Tyr Glu Glu
385                 390                 395                 400

Trp Leu Leu Asn Glu Ile Arg Arg Leu Glu Arg Leu Asp His Leu Ala
                405                 410                 415

Glu Lys Phe Arg Gln Lys Ala Ser Ile His Glu Ala Trp Thr Asp Gly
            420                 425                 430

Lys Glu Ala Met Leu Lys Gln Arg Asp Tyr Glu Thr Ala Thr Leu Ser
        435                 440                 445

Asp Ile Lys Ala Leu Ile Arg Lys His Glu Ala Phe Glu Ser Asp Leu
    450                 455                 460

Ala Ala His Gln Asp Arg Val Glu Gln Ile Ala Ala Ile Ala Gln Glu
465                 470                 475                 480

Leu Asn Glu Leu Asp Tyr Tyr Asp Ser His Asn Val Asn Thr Arg Cys
                485                 490                 495

Gln Lys Ile Cys Asp Gln Trp Asp Asn Leu Gly Ser Leu Thr His Ser
            500                 505                 510

Arg Arg Glu Ala Leu Glu Lys Thr Glu Lys Gln Leu Glu Thr Ile Asp
        515                 520                 525

Gln Leu His Leu Glu Tyr Ala Lys Arg Ala Ala Pro Phe Asn Asn Trp
    530                 535                 540

Met Glu Ser Ala Met Glu Asp Leu Gln Asp Met Phe Ile Val His Thr
545                 550                 555                 560

Ile Glu Glu Ile Glu Gly Leu Ile Ser Ala His Asp Gln Phe Lys Ser
                565                 570                 575

Thr Leu Pro Asp Ala Asp Arg Glu Arg Glu Ala Ile Leu Ala Ile His
            580                 585                 590

Lys Glu Ala Gln Arg Ile Ala Glu Ser Asn His Ile Lys Leu Ser Gly
        595                 600                 605

Ser Asn Pro Tyr Thr Thr Val Thr Pro Gln Ile Ile Asn Ser Lys Trp
    610                 615                 620
```

```
Glu Lys Val Gln Gln Leu Val Pro Lys Arg Asp His Ala Leu Leu Glu
625                 630                 635                 640

Glu Gln Ser Lys Gln Gln Ser Asn Glu His Leu Arg Arg Gln Phe Ala
                645                 650                 655

Ser Gln Ala Asn Met Val Gly Pro Trp Ile Gln Thr Lys Met Glu Glu
            660                 665                 670

Ile Gly Arg Ile Ser Ile Glu Met Asn Gly Thr Leu Glu Asp Gln Leu
        675                 680                 685

Ser His Leu Lys Gln Tyr Glu Arg Ser Ile Val Asp Tyr Lys Pro Ser
    690                 695                 700

Leu Asp Leu Leu Glu Gln Gln His Gln Leu Ile Gln Glu Ala Leu Ile
705                 710                 715                 720

Phe Asp Asn Lys His Thr Asn Tyr Thr Met Glu His Ile Arg Val Gly
                725                 730                 735

Trp Glu Gln Leu Leu Thr Thr Ile Ala Arg Thr Ile Asn Glu Val Glu
            740                 745                 750

Asn Gln Ile Leu Thr Arg Asp Ala Lys Gly Ile Ser Gln Glu Gln Met
        755                 760                 765

Gln Glu Phe Arg Ala Ser Phe Asn His Phe Asp Lys Asp His Gly Gly
    770                 775                 780

Ala Leu Gly Pro Glu Glu Phe Lys Ala Cys Leu Ile Ser Leu Gly Tyr
785                 790                 795                 800

Asp Val Glu Asn Asp Arg Gln Gly Asp Ala Glu Phe Asn Arg Ile Met
                805                 810                 815

Ser Val Val Asp Pro Asn His Ser Gly Leu Val Thr Phe Gln Ala Phe
            820                 825                 830

Ile Asp Phe Met Ser Arg Glu Thr Thr Asp Thr Asp Thr Ala Asp Gln
        835                 840                 845

Val Ile Ala Ser Phe Lys Val Leu Ala Gly Asp Lys Asn Phe Ile Thr
    850                 855                 860

Ala Glu Glu Leu Arg Arg Glu Leu Pro Pro Asp Gln Ala Glu Tyr Cys
865                 870                 875                 880

Ile Ala Arg Met Ala Pro Tyr Gln Gly Pro Asp Ala Ala Pro Gly Ala
                885                 890                 895

Leu Asp Tyr Lys Ser Phe Ser Thr Ala Leu Tyr Gly Glu Ser Asp Leu
            900                 905                 910
```

```
<210> SEQ ID NO 27
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 27

gctagcatgg atgacgatat cgctgcgctg gtcgt                            35


<210> SEQ ID NO 28
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 28

ctcgaggaag cacttgcggt gcacgatgga g                                31
```

<210> SEQ ID NO 29
<211> LENGTH: 3438
<212> TYPE: DNA
<213> ORGANISM: Artificial sequence
<220> FEATURE:
<223> OTHER INFORMATION: Murine Beta-Actin-Ig fusion protein coding sequence

<400> SEQUENCE: 29
atggtggact accacgcagc gaaccaggcg taccagtacg gcccgaacag cggcggcggc 60
aatggcgcgg gtggcggcgg aagcatgggc gactacatgg cccaggagga tgactgggac 120
cgggacctgc tgttggaccc ggcctgggag aagcagcagc gcaagacctt cacagcctgg 180
tgcaactctc atcttcggaa ggctggcact cagatcgaga atatcgatga ggacttcagg 240
gatgggctca aacttatgct tctgttggag gtcatttcag gggagcgttt gcctaagcca 300
gagcggggga agatgcgagt gcacaagatc aacaatgtaa acaaagccct ggacttcatc 360
gccagcaagg gagtcaagct ggtgtccatc ggggcagaag agattgtgga tggcaatgca 420
aagatgaccc tgggaatgat ctggaccatc atcctcagat ttgccatcca ggacatctct 480
gtggaagaga cctctgctaa ggaaggactc ctcctctggt gccagagaaa gacagcccca 540
tataaaaacg tcaacgtcca gaacttccat atcagctgga aggacgggct ggccttcaat 600
gcactcatcc accggcacag gcctgagctg attgagtatg acaagctgcg gaaggatgat 660
ccagtcacca acctaaacaa tgcatttgaa gtggctgaga aatacctcga tatccccaag 720
atgttggatg ctgaggacat cgtgaacaca gcccggcccg acgagaaggc cataatgaca 780
tatgtgtcca gcttctacca tgccttttca ggagcgcaga aggctgagac cgctgccaac 840
cggatctgca aggtgctggc tgtgaaccag gaaaatgagc acctgatgga agactatgaa 900
cgcctggcca gtgatcttct agagtggatt cggcgcacca tcccctggct ggaggaccgg 960
gtgcctcaga agaccatcca ggaaatgcag cagaagctgg aggacttccg agactatagg 1020
cgtgtgcaca agccgcccaa ggtgcaggag aagtgtcagc tggagatcaa cttcaacaca 1080
ctgcagacca agctgcggct cagcaaccgg cctgccttca tgccctccga gggcaggatg 1140
gtctccgaca tcaacaatgg atggcagcac ctggagcagg ctgagaaggg ctatgaagaa 1200
tggctgctga atgaaatccg taggctggaa cggcttgacc acctggcaga gaagttccgg 1260
cagaaggctt ccatccacga ggcctggact gatgggaagg aggccatgct gaagcaacgg 1320
gactacgaga cagccaccct gtcagacatc aaagctctga tccgaaaaca tgaggccttt 1380
gaaagtgacc tggctgcaca ccaggaccga gtggagcaga ttgctgcaat tgctcaggag 1440
ctcaacgagc tggactacta tgactcccac aacgtcaaca cacggtgcca gaagatctgc 1500
gaccagtggg ataacctggg ctctctgaca cacagtcgca gggaagcctt ggagaaaaca 1560
gagaaacagc tagagaccat cgaccagcta catttggagt atgccaagcg ggctgcaccc 1620
ttcaacaact ggatggagag tgccatggag gacctgcagg acatgttcat cgtccacacc 1680
atcgaggaga tcgagggcct gatctcagcc catgaccagt tcaagtccac cctgccagat 1740
gctgacaggg agcgtgaggc catcctggcc atccacaagg aggcccagag gatcgctgag 1800
agcaatcaca tcaagctgtc gggcagcaat ccctacacca ctgttacccc ccagatcatc 1860
aactccaagt gggagaaggt gcagcagctg gtgccaaaga gggaccatgc actcctggag 1920
gagcagagca agcagcaatc caatgagcac cttcgccgac agttcgccag ccaagccaat 1980
atggtggggc cgtggatcca gaccaagatg gaggagatcg ggcgcatctc cattgagatg 2040
aacgggactc tggaagacca gctgagccac ctgaagcagt acgagcgcag catcgtggac 2100

-continued

```
tacaagccca gcctggacct gctggagcag cagcaccagc tcatccagga ggccctcatc   2160

ttcgacaaca agcacaccaa ctacacaatg gagcatatcc gtgtgggctg ggagcagctg   2220

ctcacgacca ttgcccgcac catcaatgag gtggaaaacc agatcctcac ccgagatgcc   2280

aagggtatca gccaggagca gatgcaggag ttccgggcat ccttcaacca ttttgacaag   2340

gaccatggcg gggcactggg gcctgaggaa ttcaaggcct gcctcatcag cctgggctat   2400

gacgtggaga atgaccggca gggtgatgct gagttcaacc ggatcatgag tgtggttgat   2460

cccaaccata gtggcctcgt gaccttccaa gccttcattg acttcatgtc aagggagacc   2520

acagacacag acacagctga tcaggtcatc gcctccttca aggtcctggc aggagacaag   2580

aacttcatca ctgctgagga actgcggaga gagctgcccc ccgaccaggc cgagtactgc   2640

atcgcccgca tggcacccta ccaggggcct gatgctgctc ctggcgccct tgactacaag   2700

tccttctcca cagccctcta tggggagagc gacctgccgc tcgaggtgcc cagggattgt   2760

ggttgtaagc cttgcatatg tacagtccca gaagtatcat ctgtcttcat cttcccccca   2820

aagcccaagg atgtgctcac cattactctg actcctaagg tcacgtgtgt tgtggtagac   2880

atcagcaagg atgatcccga ggtccagttc agctggtttg tagatgatgt ggaggtgcac   2940

acagctcaga cgcaaccccg ggaggagcag ttcaacagca ctttccgctc agtcagtgaa   3000

cttcccatca tgcaccagga ctgcctcaat ggcaaggagt tcaaatgcag ggtcaacagt   3060

gcagctttcc ctgcccccat cgagaaaacc atctccaaaa ccaaaggcag accgaaggct   3120

ccacaggtgt acaccattcc acctcccaag gagcagatgg ccaaggataa agtcagtctg   3180

acctgcatga taacagactt cttccctgaa gacattactg tggagtggca gtggaatggg   3240

cagccagcgg agaactacaa gaacactcag cccatcatgg acacagatgg ctcttacttc   3300

gtctacagca agctcaatgt gcagaagagc aactgggagg caggaaatac tttcacctgc   3360

tctgtgttac atgagggcct gcacaaccac catactgaga agagcctctc ccactctcct   3420

ggtaaagggc ccgaacaa                                                 3438
```

```
<210> SEQ ID NO 30
<211> LENGTH: 1146
<212> TYPE: PRT
<213> ORGANISM: Artificial sequence
<220> FEATURE:
<223> OTHER INFORMATION: Murine Beta-Actin-Ig fusion protein

<400> SEQUENCE: 30

Met Val Asp Tyr His Ala Ala Asn Gln Ala Tyr Gln Tyr Gly Pro Asn
1               5                   10                  15

Ser Gly Gly Gly Asn Gly Ala Gly Gly Gly Gly Ser Met Gly Asp Tyr
            20                  25                  30

Met Ala Gln Glu Asp Asp Trp Asp Arg Asp Leu Leu Leu Asp Pro Ala
        35                  40                  45

Trp Glu Lys Gln Gln Arg Lys Thr Phe Thr Ala Trp Cys Asn Ser His
    50                  55                  60

Leu Arg Lys Ala Gly Thr Gln Ile Glu Asn Ile Asp Glu Asp Phe Arg
65                  70                  75                  80

Asp Gly Leu Lys Leu Met Leu Leu Leu Glu Val Ile Ser Gly Glu Arg
                85                  90                  95

Leu Pro Lys Pro Glu Arg Gly Lys Met Arg Val His Lys Ile Asn Asn
            100                 105                 110

Val Asn Lys Ala Leu Asp Phe Ile Ala Ser Lys Gly Val Lys Leu Val
        115                 120                 125
```

-continued

```
Ser Ile Gly Ala Glu Glu Ile Val Asp Gly Asn Ala Lys Met Thr Leu
    130                 135                 140

Gly Met Ile Trp Thr Ile Ile Leu Arg Phe Ala Ile Gln Asp Ile Ser
145                 150                 155                 160

Val Glu Glu Thr Ser Ala Lys Glu Gly Leu Leu Leu Trp Cys Gln Arg
                165                 170                 175

Lys Thr Ala Pro Tyr Lys Asn Val Asn Val Gln Asn Phe His Ile Ser
            180                 185                 190

Trp Lys Asp Gly Leu Ala Phe Asn Ala Leu Ile His Arg His Arg Pro
        195                 200                 205

Glu Leu Ile Glu Tyr Asp Lys Leu Arg Lys Asp Asp Pro Val Thr Asn
    210                 215                 220

Leu Asn Asn Ala Phe Glu Val Ala Glu Lys Tyr Leu Asp Ile Pro Lys
225                 230                 235                 240

Met Leu Asp Ala Glu Asp Ile Val Asn Thr Ala Arg Pro Asp Glu Lys
                245                 250                 255

Ala Ile Met Thr Tyr Val Ser Ser Phe Tyr His Ala Phe Ser Gly Ala
            260                 265                 270

Gln Lys Ala Glu Thr Ala Ala Asn Arg Ile Cys Lys Val Leu Ala Val
        275                 280                 285

Asn Gln Glu Asn Glu His Leu Met Glu Asp Tyr Glu Arg Leu Ala Ser
    290                 295                 300

Asp Leu Leu Glu Trp Ile Arg Arg Thr Ile Pro Trp Leu Glu Asp Arg
305                 310                 315                 320

Val Pro Gln Lys Thr Ile Gln Glu Met Gln Gln Lys Leu Glu Asp Phe
                325                 330                 335

Arg Asp Tyr Arg Arg Val His Lys Pro Pro Lys Val Gln Glu Lys Cys
            340                 345                 350

Gln Leu Glu Ile Asn Phe Asn Thr Leu Gln Thr Lys Leu Arg Leu Ser
        355                 360                 365

Asn Arg Pro Ala Phe Met Pro Ser Glu Gly Arg Met Val Ser Asp Ile
    370                 375                 380

Asn Asn Gly Trp Gln His Leu Glu Gln Ala Glu Lys Gly Tyr Glu Glu
385                 390                 395                 400

Trp Leu Leu Asn Glu Ile Arg Arg Leu Glu Arg Leu Asp His Leu Ala
                405                 410                 415

Glu Lys Phe Arg Gln Lys Ala Ser Ile His Glu Ala Trp Thr Asp Gly
            420                 425                 430

Lys Glu Ala Met Leu Lys Gln Arg Asp Tyr Glu Thr Ala Thr Leu Ser
        435                 440                 445

Asp Ile Lys Ala Leu Ile Arg Lys His Glu Ala Phe Glu Ser Asp Leu
    450                 455                 460

Ala Ala His Gln Asp Arg Val Glu Gln Ile Ala Ala Ile Ala Gln Glu
465                 470                 475                 480

Leu Asn Glu Leu Asp Tyr Tyr Asp Ser His Asn Val Asn Thr Arg Cys
                485                 490                 495

Gln Lys Ile Cys Asp Gln Trp Asp Asn Leu Gly Ser Leu Thr His Ser
            500                 505                 510

Arg Arg Glu Ala Leu Glu Lys Thr Glu Lys Gln Leu Glu Thr Ile Asp
        515                 520                 525

Gln Leu His Leu Glu Tyr Ala Lys Arg Ala Ala Pro Phe Asn Asn Trp
    530                 535                 540

Met Glu Ser Ala Met Glu Asp Leu Gln Asp Met Phe Ile Val His Thr
545                 550                 555                 560
```

```
Ile Glu Glu Ile Glu Gly Leu Ile Ser Ala His Asp Gln Phe Lys Ser
                565                 570                 575

Thr Leu Pro Asp Ala Asp Arg Glu Arg Glu Ala Ile Leu Ala Ile His
            580                 585                 590

Lys Glu Ala Gln Arg Ile Ala Glu Ser Asn His Ile Lys Leu Ser Gly
        595                 600                 605

Ser Asn Pro Tyr Thr Thr Val Thr Pro Gln Ile Ile Asn Ser Lys Trp
    610                 615                 620

Glu Lys Val Gln Gln Leu Val Pro Lys Arg Asp His Ala Leu Leu Glu
625                 630                 635                 640

Glu Gln Ser Lys Gln Gln Ser Asn Glu His Leu Arg Arg Gln Phe Ala
                645                 650                 655

Ser Gln Ala Asn Met Val Gly Pro Trp Ile Gln Thr Lys Met Glu Glu
            660                 665                 670

Ile Gly Arg Ile Ser Ile Glu Met Asn Gly Thr Leu Glu Asp Gln Leu
        675                 680                 685

Ser His Leu Lys Gln Tyr Glu Arg Ser Ile Val Asp Tyr Lys Pro Ser
    690                 695                 700

Leu Asp Leu Leu Glu Gln Gln His Gln Leu Ile Gln Glu Ala Leu Ile
705                 710                 715                 720

Phe Asp Asn Lys His Thr Asn Tyr Thr Met Glu His Ile Arg Val Gly
                725                 730                 735

Trp Glu Gln Leu Leu Thr Thr Ile Ala Arg Thr Ile Asn Glu Val Glu
            740                 745                 750

Asn Gln Ile Leu Thr Arg Asp Ala Lys Gly Ile Ser Gln Glu Gln Met
        755                 760                 765

Gln Glu Phe Arg Ala Ser Phe Asn His Phe Asp Lys Asp His Gly Gly
    770                 775                 780

Ala Leu Gly Pro Glu Glu Phe Lys Ala Cys Leu Ile Ser Leu Gly Tyr
785                 790                 795                 800

Asp Val Glu Asn Asp Arg Gln Gly Asp Ala Glu Phe Asn Arg Ile Met
                805                 810                 815

Ser Val Val Asp Pro Asn His Ser Gly Leu Val Thr Phe Gln Ala Phe
            820                 825                 830

Ile Asp Phe Met Ser Arg Glu Thr Thr Asp Thr Asp Thr Ala Asp Gln
        835                 840                 845

Val Ile Ala Ser Phe Lys Val Leu Ala Gly Asp Lys Asn Phe Ile Thr
    850                 855                 860

Ala Glu Glu Leu Arg Arg Glu Leu Pro Pro Asp Gln Ala Glu Tyr Cys
865                 870                 875                 880

Ile Ala Arg Met Ala Pro Tyr Gln Gly Pro Asp Ala Ala Pro Gly Ala
                885                 890                 895

Leu Asp Tyr Lys Ser Phe Ser Thr Ala Leu Tyr Gly Glu Ser Asp Leu
            900                 905                 910

Pro Leu Glu Val Pro Arg Asp Cys Gly Cys Lys Pro Cys Ile Cys Thr
        915                 920                 925

Val Pro Glu Val Ser Ser Val Phe Ile Phe Pro Pro Lys Pro Lys Asp
    930                 935                 940

Val Leu Thr Ile Thr Leu Thr Pro Lys Val Thr Cys Val Val Val Asp
945                 950                 955                 960

Ile Ser Lys Asp Asp Pro Glu Val Gln Phe Ser Trp Phe Val Asp Asp
                965                 970                 975

Val Glu Val His Thr Ala Gln Thr Gln Pro Arg Glu Glu Gln Phe Asn
            980                 985                 990
```

-continued

```
Ser Thr Phe Arg Ser Val Ser Glu  Leu Pro Ile Met His  Gln Asp Cys
        995                 1000                 1005

Leu Asn  Gly Lys Glu Phe Lys  Cys Arg Val Asn Ser  Ala Ala Phe
    1010                 1015                 1020

Pro Ala  Pro Ile Glu Lys Thr  Ile Ser Lys Thr Lys  Gly Arg Pro
    1025                 1030                 1035

Lys Ala  Pro Gln Val Tyr Thr  Ile Pro Pro Pro Lys  Glu Gln Met
    1040                 1045                 1050

Ala Lys  Asp Lys Val Ser Leu  Thr Cys Met Ile Thr  Asp Phe Phe
    1055                 1060                 1065

Pro Glu  Asp Ile Thr Val Glu  Trp Gln Trp Asn Gly  Gln Pro Ala
    1070                 1075                 1080

Glu Asn  Tyr Lys Asn Thr Gln  Pro Ile Met Asp Thr  Asp Gly Ser
    1085                 1090                 1095

Tyr Phe  Val Tyr Ser Lys Leu  Asn Val Gln Lys Ser  Asn Trp Glu
    1100                 1105                 1110

Ala Gly  Asn Thr Phe Thr Cys  Ser Val Leu His Glu  Gly Leu His
    1115                 1120                 1125

Asn His  His Thr Glu Lys Ser  Leu Ser His Ser Pro  Gly Lys Gly
    1130                 1135                 1140

Pro Glu  Gln
    1145


<210> SEQ ID NO 31
<211> LENGTH: 21
<212> TYPE: PRT
<213> ORGANISM: Artificial sequence
<220> FEATURE:
<223> OTHER INFORMATION: Myelin oligodendrocyte glycoprotein peptide
      (MOG)p35-55

<400> SEQUENCE: 31

Met Glu Val Gly Trp Tyr Arg Ser Pro Phe Ser Arg Val Val His Leu
1               5                   10                  15

Tyr Arg Asn Gly Lys
            20
```